US010130711B2

(12) United States Patent
Mejia Oneto et al.

(10) Patent No.: US 10,130,711 B2
(45) Date of Patent: Nov. 20, 2018

(54) CHEMICAL STRUCTURES FOR LOCALIZED DELIVERY OF THERAPEUTIC AGENTS

(71) Applicants: The Regents of the University of California, Oakland, CA (US); Alchemcial Research Holdings, LLC, Allentown, PA (US)

(72) Inventors: Jose Manuel Mejia Oneto, Davis, CA (US); Ziyad F. Al-Rashid, Allentown, PA (US)

(73) Assignees: The Regents of the University of California, Oakland, CA (US); Alchemical Research Holdings, LLC, Allentown, PA (US)

( * ) Notice: Subject to any disclaimer, the term of this patent is extended or adjusted under 35 U.S.C. 154(b) by 0 days.

(21) Appl. No.: 14/899,041

(22) PCT Filed: Jun. 18, 2014

(86) PCT No.: PCT/US2014/043020
§ 371 (c)(1),
(2) Date: Dec. 16, 2015

(87) PCT Pub. No.: WO2014/205126
PCT Pub. Date: Dec. 24, 2014

(65) Prior Publication Data
US 2016/0120987 A1 May 5, 2016

Related U.S. Application Data

(60) Provisional application No. 61/836,800, filed on Jun. 19, 2013.

(51) Int. Cl.
| | | |
|---|---|---|
| *A61K 31/495* | (2006.01) | |
| *A61K 31/015* | (2006.01) | |
| *A61K 47/36* | (2006.01) | |
| *C07D 257/08* | (2006.01) | |
| *C07C 13/263* | (2006.01) | |
| *A61K 9/00* | (2006.01) | |
| *A61K 49/00* | (2006.01) | |
| *A61K 38/14* | (2006.01) | |
| *A61K 31/7042* | (2006.01) | |
| *A61K 47/54* | (2017.01) | |

(52) U.S. Cl.
CPC ............ *A61K 47/36* (2013.01); *A61K 9/0024* (2013.01); *A61K 31/015* (2013.01); *A61K 31/495* (2013.01); *A61K 31/7042* (2013.01); *A61K 38/14* (2013.01); *A61K 47/545* (2017.08); *A61K 47/555* (2017.08); *A61K 49/0002* (2013.01); *C07C 13/263* (2013.01); *C07D 257/08* (2013.01)

(58) Field of Classification Search
None
See application file for complete search history.

(56) References Cited

U.S. PATENT DOCUMENTS

| | | | |
|---|---|---|---|
| 5,770,229 A * | 6/1998 | Tanihara | A61K 47/48784 424/488 |
| 8,552,183 B2 | 10/2013 | Wiessler et al. | |
| 9,421,274 B2 | 8/2016 | Robillard et al. | |
| 9,427,482 B2 * | 8/2016 | Rossin | A61K 47/4873 |
| 9,463,256 B2 | 10/2016 | Lub et al. | |
| 2005/0014197 A1 | 1/2005 | Agnew et al. | |
| 2009/0023916 A1 | 1/2009 | Fox et al. | |
| 2011/0223257 A1 | 9/2011 | Zhao et al. | |
| 2011/0268654 A1 | 11/2011 | Hilderbrand et al. | |
| 2012/0034161 A1 | 2/2012 | Robillard et al. | |
| 2012/0076727 A1 | 3/2012 | McBride et al. | |
| 2013/0281644 A1 | 10/2013 | Kiessling et al. | |
| 2014/0199331 A1 | 7/2014 | Robillard et al. | |
| 2016/0114046 A1 | 4/2016 | Brudno et al. | |
| 2017/0087258 A1 | 3/2017 | Oneto et al. | |
| 2017/0095580 A1 | 4/2017 | Mejia Oneto et al. | |

FOREIGN PATENT DOCUMENTS

| | | |
|---|---|---|
| EP | 1867638 A1 | 12/2007 |
| EP | 2719400 A2 | 4/2014 |
| WO | WO-03/000708 A1 | 1/2003 |
| WO | 2010/051530 A2 | 5/2010 |
| WO | 2011/127149 A1 | 10/2011 |
| WO | 2012/012612 A2 | 1/2012 |
| WO | 2012/049624 A1 | 4/2012 |
| WO | 2012/074840 A2 | 6/2012 |

(Continued)

OTHER PUBLICATIONS

Thomas et al., "Polyvalent Dendrimer-Methotrexate as a Folate Receptor-Targeted Cancer Therapeutic" Molecular Pharmaceutics (2012) vol. 9 pp. 2669-2676.*
Antoci, Jr., et al., "The inhibition of *Staphylococus epidermidis* biofilm formation by vancomycin-modified titanium alloy and implications for the treatment of periprosthetic infection," *Biomaterials*, vol. 29, pp. 4684-4690.
Rossin, et al., "In Vivo Chemistry for Pretargeted Tumor Imagining in Live Mice," *Angew. Chem. Int. Ed.*, vol. 49, pp. 3375-3378 (2010).
Rossin, et al., Supporting Information for "In Vivo Chemistry for Pretargeted Tumor Imagining in Live Mice," Sections S1-S6, pp. S2-S21 (2010).
Royzen, et al., "A Photochemical Synthesis of Functionalized trans-Cyclooctenes Driven by Metal Composition," *J. Am. Chem. Soc.* vol. 130, pp. 3760-3761 (2008).

(Continued)

*Primary Examiner* — Eric Olson
(74) *Attorney, Agent, or Firm* — Mintz, Levin, Cohn, Ferris, Glovsky and Popeo, P.C.

(57) ABSTRACT

The present invention provides a method for selective delivery of a therapeutic or diagnostic agent to a targeted organ or tissue by implanting a biocompatible solid support in the patient being linked to a first binding agent, and administering a second binding agent to the patient linked to the therapeutic or diagnostic agent, such that the therapeutic or diagnostic agent accumulates at the targeted organ or tissue.

9 Claims, 16 Drawing Sheets

(56) References Cited

FOREIGN PATENT DOCUMENTS

| WO | 2012/085789 A1 | 6/2012 | |
|---|---|---|---|
| WO | 2012/0156918 A1 | 11/2012 | |
| WO | 2012/156919 A1 | 11/2012 | |
| WO | 2012/156920 A1 | 11/2012 | |
| WO | 2012153254 A1 | 11/2012 | |
| WO | 2012/0168512 A2 | 12/2012 | |
| WO | 2012165462 A1 | 12/2012 | |
| WO | 2014/065860 A1 | 5/2014 | |
| WO | 2014/081299 A1 | 5/2014 | |
| WO | 2014/081300 A1 | 5/2014 | |
| WO | 2014/081301 A1 | 5/2014 | |
| WO | 2014/081303 A1 | 5/2014 | |
| WO | 2014/117001 A1 | 7/2014 | |
| WO | WO2014/117001 | * 7/2014 | ............ A61K 51/00 |
| WO | 2014/138186 A1 | 9/2014 | |
| WO | 2014/200767 A1 | 12/2014 | |
| WO | 2014/205126 A1 | 12/2014 | |
| WO | 2015/139025 A1 | 9/2015 | |
| WO | WO-2015/139025 A1 | 9/2015 | |
| WO | 2015/154082 A1 | 10/2015 | |

OTHER PUBLICATIONS

Al-Dubai, et al., "Biocompatible medical implant materials with binding sites for a biodegradable drug-delivery system," Nanotechnolopy, Science and Applications, vol. 2011, No. 4, pp. 87-94 (2011).

Kharkar, et al., "Designing degradable hydrogels for orthogonal control of cell microenvironments," Chem. Soc. Rev., vol. 42, No. 17, pp. 7335-7372 (2013).

Li, et al.,"Monodispersed PEG-DOT A Conjugated Anti-Tag-72 Diabody Has Low Kidney Uptake and High Tumor to Blood Ratios Resulting in Improvesd $^{64}$Cu PET Imaging," J. Nucl. Med., vol. 51, No. 7, pp. 1139-1146.

Oneto, et al, "Implantable biomaterial based on click chemistry for targeting small molecules," Acta Biomaterialia, pp. 1-7 (2014).

Reiner et al. "The inverse electron demand Diels-Alder click reaction in radiochemistry," J. Labelled Comp. Radiopharm., vol. 57, No. 4, pp. 285-290 (2014).

Zeglis, et al, "A Pretargeted PET Imaging Strategy Based on Bioorthogonal Diels-Alder Click Chemistry," J. Nucl. Med., vol. 54, No. 8, pp. 1389-1396 (2013).

International Search Report for International Application No. PCT/US2014/043020 dated Oct. 6, 2014.

Altin et al., "Fabrication of "Clickable" Hydrogels via Dendron-Polymer Conjugates," Macromolecules, 2010, vol. 43, No. 8, pp. 3801-3808.

Blackman et al., "Tetrazine Ligation: Fast Bioconjugation Based on Inverse-Electron-Demand Diels-Alder Reactivity," J. Am. Chem. Soc., 2008, vol. 130, pp. 13518-13519.

Brudno et al., "In Vivo Targeting through Click Chemistry," Chem. Med. Chem., 2015, vol. 10, pp. 617-620.

Brudno et al., "On-demand drug delivery from local depots," J. Control. Release, 2015, http://dx.doi.org/10.1016/j.jconrel.2015.09.011, 10 pages.

Burdick et al., Acellular Biomaterials: An Evolving Alternative to Cell-Based Therapies, Science Translation Medicine, Mar. 13, 2013, vol. 5, Issue 176, 4 pages.

Chung et al., "Ubiquitous Detection of Gram-Positive Bacteria with Bioorthogonal Magnetofluorescent Nanoparticles," ASC NANO, 2011, vol. 5, No. 11, pp. 8834-8841.

Coviello et al., "Polysaccharide hydrogels for modified release formulations," Journal of Controlled Release, 2007, vol. 119, pp. 5-24.

Deforest et al., "Sequential click reactions for synthesizing and patterning three-dimensional cell microenvironments," Nature materials: Letters, Aug. 2009, vol. 8, pp. 659-664.

Desai et al., "Versatile click alginate hydrogels crosslinked via tetrazineenorbornene chemistry," Biomaterials, 2015, vol. 50, pp. 30-37.

Devaraj et al., "Fast and Sensitive Pretargeted Labeling of Cancer Cells through a Tetrazine/trans-Cyclooctene Cycloaddition," Angew. Chem. Int. Ed., 2009, vol. 48, pp. 7013-7016.

Devaraj et al., "Reactive polymer enables efficient in vivo bioorthogonal chemistry," PNAS, Mar. 27, 2012, vol. 109, No. 13, pp. 4762-4767.

Eckhouse et al., "Local Hydrogel Release of Recombinant TIMP-3 Attenuates Adverse Left Ventricular Remodeling After Experimental Myocardial Infarction," Science Translation Medicine, Feb. 12, 2014, vol. 6, Issue 223, 10 pages.

Eschenhagen et al., "Physiological aspects of cardiac tissue engineering," Am. J. Physiol. Heart Circ. Physiol., vol. 30, 2012, pp. H133-H143.

European Application No. 14813532.0, Extended European Search Report dated Dec. 2, 2016, 10 pages.

International Application No. PCT/US2015/020718 , "International Search Report and Written Opinion", dated Jun. 10, 2015, 8 pages.

Koo et al., "Bioorthogonal Copper-Free Click Chemistry In Vivo for Tumor-Targeted Delivery of Nanoparticles," Angew. Chem. Int. Ed., 2012, vol. 51, pp. 11836-11840.

Koshy et al., "Click-Crosslinked Injectable Gelatin Hydrogels," Advanced Healthcare Materials, 2016, DOI: 10.1002/adhm.201500757, 7 pages.

Landa et al., "Effect of Injectable Alginate Implant on Cardiac Remodeling and Function After Recent and Old Infarcts in Rat," Circulation, Mar. 18, 2008, vol. 17, pp. 1388-1396.

Li et al., "Diels-Alder reaction-triggered bioorthogonal protein decaging in living cells," Natural Chemical Biology, Advanced Online Publication, Nov. 2, 2014, DOI:10.1038/NCHEMBIO.1656.

Matikonda et al., "Bioorthogonal prodrug activation driven by a strain-promoted 1,3-dipolar cycloaddition," Chem. Sci., 2015, vol. 6, pp. 1212-1218.

Mejia Oneto et al., "Implantable biomaterial based on click chemistry for targeting small molecules," Acta Biomaterialia, 2014, vol. 10, pp. 5099-5105.

Neves et al., "Imaging Cell Surface Glycosylation in Vivo Using "Double Click" Chemistry," Bioconjugate Chem., May 5, 2013, vol. 24, pp. 934-941.

Patterson et al., "Finding the Right (Bioorthogonal) Chemistry," ACS Chem. Biol., 2014, vol. 9, pp. 592-605.

Pretze et al., "Recent Trends in Bioorthogonal Click-Radiolabeling Reactions Using Fluorine-18", Molecules, vol. 18, Jul. 22, 2013, pp. 8618-8665; doi:10.3390/molecules18078618.

Seif-Naraghi et al., "Safety and Efficacy of an Injectable Extracellular Matrix Hydrogel for Treating Myocardial Infarction," Science Translation Medicine, Feb. 20, 2013, vol. 5, Issue 173, 10 pages.

Selvaraj et al., "Tetrazine-tans -cyclooctene ligation for the rapid construction of integrin αvβ$^3$ targeted PET tracer based on a cyclic RGD peptide," Bioorg. Med. Chem. Lett., Sep. 1, 2011; 21(17), pp. 5011-5014; doi:10.1016/j.bmcl.2011.04.116.

Selvaraj et al., "trans-Cyclooctene—a stable, voracious dienophile for bioorthogonal labeling", Current Opinion in Chemical Biology, vol. 17, Issue 5, Oct. 2013, pp. 753-760; doi:10.1016/j.cbpa.2013.07.031.

Shelke et al., "Polysaccharide biomaterials for drug delivery and regenerative engineering," Polym. Adv. Technol., 2014, vol. 25, pp. 448-460; DOI: 10.1002/pat.3266.

Thalhammer et al., Reaktivitat Einfacher Offenkettiger Und Cyclischer Dienophile Bei Diels-Alder-Reaktionen Mit Inversem Elektronenbedarf, Tetrahedron Letters, 1991, vol. 31, No. 47, pp. 6851-6854.

Versteegen et al., Click to Release: Instantaneous Doxorubicin Elimination upon Tetrazine Ligation, Angew. Chem. Int. Ed., 2013, vol. 52, pp. 14112-14116.

Zeglis et al. "Modular Strategy for the Construction of Radiometalated Antibodies for Positron Emission Tomography Based on Inverse Electron Demand Diels-Alder Click Chemistry," Bioconjugate Chemistry, Aug. 31, 2011, vol. 22, pp. 2048-2059.

Zeglis et al., "Building Blocks for the Construction of Bioorthogonally Reactive Peptides via Solid-Phase Peptide Synthesis," Chemistry Open Communications, 2014, vol. 3, pp. 48-53, DOI: 10.1002/open.201402000.

(56) References Cited

OTHER PUBLICATIONS

Zhang et al., "An ionically crosslinked hydrogel containing vancomycin coating on a porous scaffold for drug delivery and cell culture," *International Journal of Pharmaceuticals*, Nov. 21, 2007, vol. 353, No. 1-2, pp. 74-87.

Alge, D.L. et al. (Apr. 8, 2013, e-published Mar. 8, 2013). "Synthetically tractable click hydrogels for three-dimensional cell culture formed using tetrazine-norbornene chemistry," *Biomacromolecules* 14(4):949-953.

Cok, A.M. et al. (2013). "Synthesis of ModelNetwork Hydrogels via Tetrazine-Olefin Inverse Electron Demand Diels-Alder Cycloaddition," *Macromol Symp* 329:108-112.

Extended European Search Report dated Aug. 10, 2017, for EP Application No. 15761367.0, filed Mar. 16, 2015, 13 pages.

Godoy, C.A. et al. (2010). "Enhanced activity of an immobilized lipase promoted by site-directed chemical modification with polymers," *Process Biochemistry* 45(4):534-541.

Hashida, M. et al. (1977). "Timed-Release of Mitomycin C from Its Agarose Bead Conjugate," *Chem Pharm Bull* 25:2456-2458.

Hofmann, C.M.et al. (Sep. 2012, e-published May 24, 2012). "Targeted delivery of vancomycin to *Staphylococcus epidermidis* biofilms using a fibrinogen-derived peptide," *J Biomed Mater Res A* 100(9):2517-2525.

Kojima, T. et al. (Jun. 1978). "Antitumor activity of timed-release derivative of mitomycin C, agarose bead conjugate," *Chem Pharm Bull* 26(6):1818-1824.

Korpela, T. et al. (Mar. 1976). A simple method to introduce aldehydic function to agarose, *Anal Biochem* 71(1):322-323.

Niska, J.A. et al. (Oct. 2013, Aug. 5, 2013). "Vancomycin-rifampin combination therapy has enhanced efficacy against an experimental *Staphylococcus aureus* prosthetic joint infection," *Antimicrob Agents Chemother* 57(10):5080-5086.

Sluyterman, L.A. Ae et al. (1981). "Chromatofocusing," Journal of Chromatography 206(3):441-447.

Tritton, T.R. et al. (Jul. 16, 1982). "The anticancer agent adriamycin can be actively cytotoxic without entering cells," *Science* 217(4556):248-250.

\* cited by examiner

CHEMICAL STRUCTURES FOR LOCALIZED DELIVERY OF THERAPEUTIC AGENTS

CROSS-REFERENCES TO RELATED APPLICATIONS

This application is the U.S. National Stage Entry under § 371 of International Application No. PCT/US2014/043020, filed Jun. 18, 2014, which claims priority to U.S. Application No. 61/836,800, filed Jun. 19, 2013, which is incorporated herein in its entirety.

STATEMENT AS TO RIGHTS TO INVENTIONS MADE UNDER FEDERALLY SPONSORED RESEARCH AND DEVELOPMENT

Not Applicable

BACKGROUND

Orthopaedic surgeons in the United States continue to seek improved therapies for the 600,000 fractures that suffer from delayed healing and the 100,000 that become nonunions. Infected nonunions remain a challenge and frequently require staged treatment protocols. The first step is removal of infected hardware, surgical debridement and placement of solid carriers preloaded with eluents (e.g. antibiotic "beads"). The second step involves systemic intravenous delivery of antibiotics. Finally, the patient undergoes a second surgical procedure for possible removal of solid carriers, definitive surgical stabilization and local delivery of therapeutics (e.g. recombinant human-Bone Morphogenetic Protein-2) and bone graft during surgery.

Current treatments face multiple challenges and are invasive. They involve repeated surgical approaches and are limited by the inability to modify the therapeutics after implantation (e.g. if the cultures show resistant organisms). Systemic administration of antibiotics is problematic secondary to the need for high blood levels to achieve therapeutic levels in the fracture environment. The side effects of these high serum levels require close monitoring to avoid major complications. This is an issue that would benefit from improved drug delivery methods.

This is far from the only issue faced by surgeons when it comes to delivery of therapies. Other problems include systemic intravenous delivery (e.g. chemotherapeutic agents for cancer or intravenous pain medications), local delivery of therapeutics at the time of surgery (e.g. recombinant human-Bone Morphogenetic Protein-2 after spine fusion), and direct injection to a joint (e.g. corticosteroid injection to a knee for osteoarthritis management). These issues would benefit from improved delivery of therapeutics, namely antibiotics, anti-inflammatory pain medications, bone healing modulators and chemotherapeutic agents. What is needed is a method of targeted delivery of the therapeutic or diagnostic agent to concentrate the agent at the site of need, thus lowering the overall dose of the therapeutic or diagnostic agent administered to the patient. Surprisingly, the present invention meets this and other needs.

BRIEF SUMMARY OF THE INVENTION

In some embodiments, the present invention provides a method for selectively delivering an effective amount of a therapeutic or diagnostic agent to a first location of a targeted organ or tissue in a patient, including the step of implanting a biocompatible solid support in the patient at the first location of the targeted organ or tissue, wherein the solid support is linked to a first binding agent, and wherein the first location of the targeted organ or tissue cannot be selectively targeted by chemical or biological targeting agents over other locations of the targeted organ or tissue in the patient. The method also includes the step of administering to the patient the therapeutic or diagnostic agent linked to a second binding agent, such that the first and second binding agents bind to one another upon contact, thereby selectively delivering the effective amount of the therapeutic or diagnostic agent to the first location of the targeted organ or tissue in the patient.

In some embodiments, the present invention provides a method of treating a disease or condition in a patient, including administering to the patient a therapeutic agent linked to a first binding agent, such that when the first binding agent contacts a second binding agent at the site of the disease or condition, the first and second binding agents bind to one another forming a therapeutically effective amount of the therapeutic agent at the site of the disease or condition, wherein the amount of the therapeutic agent administered to the patient is less than the therapeutically effective amount administered to the patient in the absence of the second binding agent.

In some embodiments, the present invention provides a composition including a biocompatible solid support and at least one cyclooctene linked to the biocompatible solid support.

In some embodiments, the present invention provides a composition including a therapeutic or diagnostic agent, a 1,2,4,5-tetrazine, and a linker, covalently linking the therapeutic or diagnostic agent to the 1,2,4,5-tetrazine.

DETAILED DESCRIPTION

I. General

Figure 1:
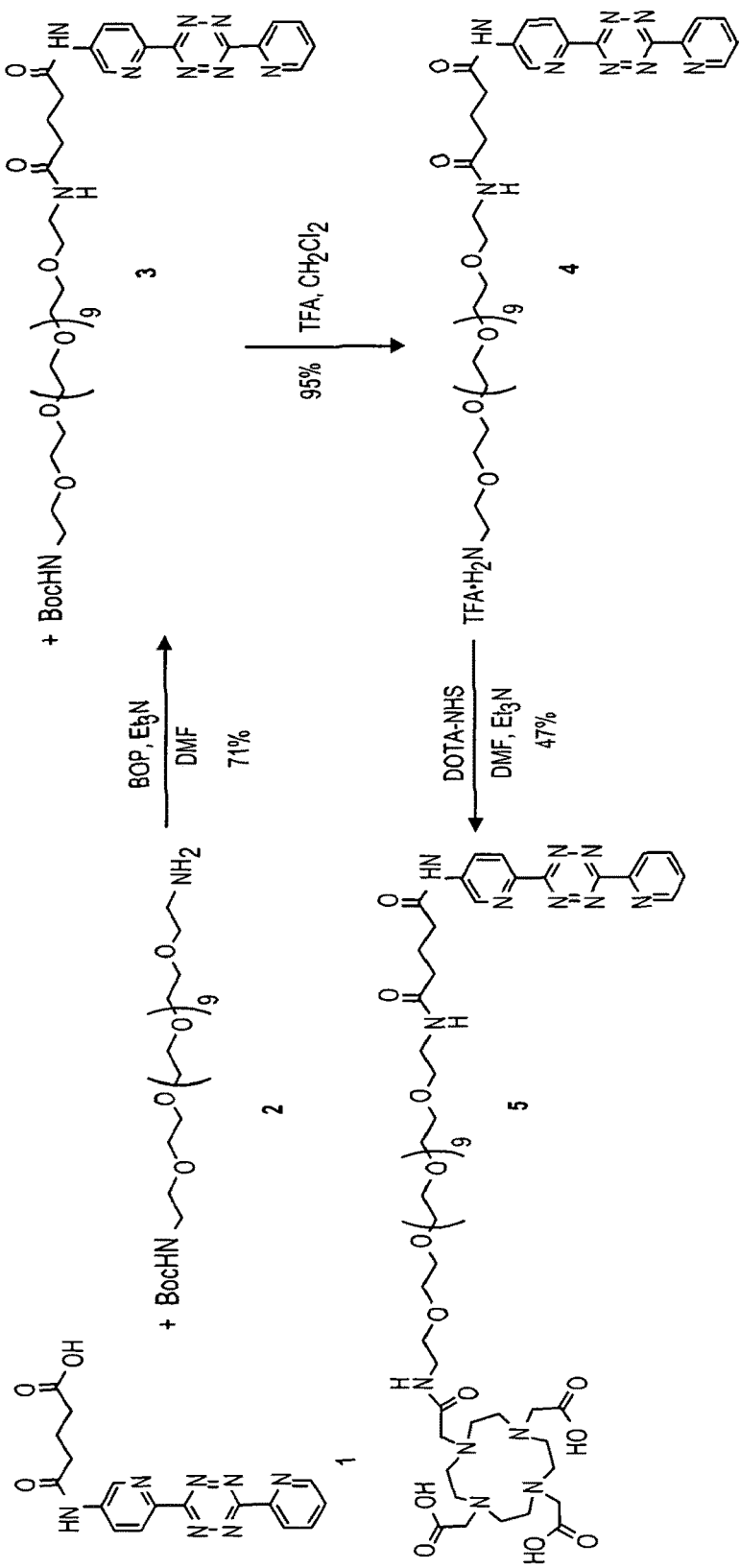
FIG. 1 shows the preparation of a tetrazine-linked therapeutic agent.

The present invention provides a method and compositions for selectively targeting portions of organs or tissue that cannot be chemically or biologically distinguished from other portions of the same organ or tissue that is not being targeted. The method involves implanting in a patient a reporter, a binding agent linked to a biocompatible solid support. The binding agent implanted in the patient is one-half of a pair of binding agents having a very high reaction rate with each other. The reporter is implanted at a particular site of an organ or tissue that is not chemically or biologically distinguished from other, non-targeted, sites of the same organ or tissue. The second binding agent covalently linked to the therapeutic or diagnostic agent, the probe, is then administered to the patient. When the two binding agents of the reporter and probe come into contact, the reaction is rapid, and a covalent bond is formed, thus covalently linking the therapeutic or diagnostic agent at the targeted site of the organ or tissue. Accordingly, a therapeutically effective amount of the therapeutic or diagnostic agent can be selectively delivered to the targeted site of the organ or tissue in the patient.

II. Definitions

"Selectively delivering" refers to delivering a therapeutic or diagnostic agent to a portion of an organ or tissue in need of treatment, without targeting other portions of the organ or tissue not in need of treatment.

"Therapeutic agent" refers to an agent capable of treating and/or ameliorating a condition or disease. Representative therapeutic agents include, but are not limited to, paclitaxel, doxorubicin, etoposide, irinotecan, SN-38, cyclosporin A, podophyllotoxin, Carmustine, Amphotericin, Ixabepilone, Patupilone (epothelone class), vancomycin, rapamycin and platinum drugs. The therapeutic agent of the present invention also include prodrug forms.

"Diagnostic agent" refers to agents that assist in diagnosing conditions or diseases. Representative diagnostic agents including imaging agents such as paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to $^{3}$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

"Targeted organ or tissue" refers to an organ or tissue that is being targeted for delivery of the therapeutic or diagnostic agent. Representative organs and tissues for targeting include those that can be targeted by chemical or biological targeting agents, as well as those organs and tissues that cannot be targeted by chemical or biological targeting agents. Representative organs or tissues include bone.

"Implanting" refers to surgical implantation into the patient's body.

"Biocompatible solid support" refers a solid support material capable of implantation into the patient's body and supporting one of the binding agents, as well as the therapeutic or diagnostic agent after the binding agents conjugate. The solid support is compatible with the patient's body. Representative biocompatible solid supports include, but are not limited to, hydrogels such as polysaccharide hydrogels, alginate, cellulose, chitosan, hyaluronic acid, chondroitin sulfate, heparin, and others.

"Contacting" or "contact" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Linker", "linked" or "linking" refers to a chemical moiety that links the compound of the present invention to a biological material that targets a specific type of cell, such as a cancer cell, other type of diseased cell, or a normal cell type. The linking can be via covalent or ionic bond formation. The linking can be direct linkage between to the two moieties being linked, or indirectly, such as via a linker. Linkers useful in the present invention can be up to 30 carbon atoms in length. Preferably, the linkers are 5-15 carbon atoms in length. The types of bonds used to link the linker to the compound and biological molecule of the present invention include, but are not limited to, amides, amines, esters, carbamates, ureas, thioethers, thiocarbamates, thiocarbonate and thioureas. One of skill in the art will appreciate that other types of bonds are useful in the present invention.

"Binding agent" refers to any group capable of forming a covalent bond to another binding agent in a biological environment. This is often referred to as bioconjugation or bioorthogonal chemistry. Representative binding agents include, but are not limited to, an amine and an activated ester, an amine and an isocyanate, an amine and an isothiocyanate, thiols for formation of disulfides, an aldehyde and amine for enamine formation, an azide for formation of an amide via a Staudinger ligation, an azide and alkyne for formation of a triazole via Click-chemistry, trans-cyclooctene (TCO) and tetrazine, and others. The binding agents useful in the present invention have a high reactivity with the corresponding binding agent so that the reaction is rapid.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Patient" refers to animals in need of treatment, such as mammals, including, but not limited to, primates (e.g., humans), cows, sheep, goats, horses, dogs, cats, rabbits, rats, mice and the like. In certain embodiments, the patient is a human.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

III. Method of Selectively Delivery of Therapeutic Agent

The present invention provides a method for selectively delivering a therapeutic agent to a location of a targeted organ or tissue in a patient. In some embodiments, the present invention provides a method for selectively delivering an effective amount of a therapeutic or diagnostic agent to a first location of a targeted organ or tissue in a patient, including the step of implanting a biocompatible solid support in the patient at the first location of the targeted organ or tissue, wherein the solid support is linked to a first binding agent, and wherein the first location of the targeted organ or tissue cannot be selectively targeted by chemical or biological targeting agents over other locations of the targeted organ or tissue in the patient. The method also includes the step of administering to the patient the therapeutic or diagnostic agent linked to a second binding agent, such that the first and second binding agents bind to one another upon contact, thereby selectively delivering the effective amount of the therapeutic or diagnostic agent to the first location of the targeted organ or tissue in the patient.

Any suitable biocompatible solid support can be used in the method of the present invention. For example, the biocompatible solid support can be a hydrogel, a cross-linked polymer matrix, a metal, a ceramic, a plastic, among others. Hydrogels useful in the present invention include, but are not limited to, polysaccharide hydrogels, alginate, cellulose, hyaluronic acid, chitosan, chitosin, chitin, hyaluronic acid, chondroitin sulfate, heparin, and others. Other sugar-based biomaterials are known in the art, such as those described in Polymer Advanced Technology 2014, 25, 448-460. Polymers useful as the biocompatible support can include, but are not limited to, polyphosphazenes, polyanhydrides, polyacetals, poly(ortho esters), polyphosphoesters, polycaprolactones, polyurethanes, polylactides, polycarbonates, polyamides, and polyethers, and blends/composites/co-polymers thereof. Representative polyethers include, but are not limited to, Poly(ethylene glycol) (PEG), polypropylene glycol) (PPG), triblock Pluronic ([PEG]n-[PPG]m-[PEG]n), PEG diacrylate (PEGDA) and PEG dimethacrylate (PEGDMA). The biocompatible solid support can also include proteins and other poly(amino acids) such as collagen, gelatin, elastin and elastin-like polypeptides, albumin, fibrin, poly(gamma-glutamic acid), poly(L-lysine), poly(L-glutamic acid), and poly(aspartic acid).

In some embodiments, the solid support can be a hydrogel. In some embodiments, the solid support can be alginate. In some embodiments, the solid support can be chitin. In some embodiments, the solid support can be hyaluronic acid. In some embodiments, the solid support can be chitosin.

Any suitable binding agent can be used in the method of the present invention. Representative binding agents can be found in "Bioconjugate Techniques" Greg T. Hermanson, 1996 and *ACS Chemical Biology* 2014, 9, 592-605. For example, binding agents useful in the method of the present invention include, but are not limited to, cyclooctene, tetrazine, azide, alkyne, amine, activated ester, isocyanate, isothiocyanate, thiol, aldehyde, amide, and others. In some embodiments, the first and second binding agents can each independently be cyclooctene, tetrazine, azide or alkyne. In some embodiments, the first and second binding agents can each independently be trans-cyclooctene or 1,2,4,5-tetrazine, such that one of the binding agents is trans-cyclooctene and the other is 1,2,4,5-tetrazine.

Any suitable organ or tissue can be targeted using the method of the present invention. Representative organs or tissues include, but are not limited to, bone, cartilage, ligaments, tendons, intestines, muscles, nervous system including brain, spinal cord, heart, and nerves, and others. For example, when the organ is the heart, the method of the present invention can be used for cardiac repair. In some embodiments, the targeted organ or tissue is bone.

Any therapeutic or diagnostic agent can be used in the method of the present invention. Representative therapeutic agents include, but are not limited to, antibiotics such as vancomycin, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. Other therapeutic agents include doxycyclin and other MMP inhibitors. In some embodiments, the therapeutic agent can be vancomycin.

Representative diagnostic agents including imaging agents such as paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to $^{3}H$, $^{11}C$, $^{13}N$, $^{18}F$, $^{19}F$, $^{60}Co$, $^{64}Cu$, $^{67}Cu$, $^{68}Ga$, $^{82}Rb$, $^{90}Sr$, $^{90}Y$, $^{99}Tc$, $^{99m}Tc$, $^{111}In$, $^{123}I$, $^{124}I$, $^{125}I$, $^{129}I$, $^{131}I$, $^{137}Cs$, $^{177}Lu$, $^{186}Re$, $^{188}Re$, $^{211}At$, Rn, Ra, Th, U, Pu and $^{241}Am$. The diagnostic agents can also include chelators such as 1,4,8,11-tetraaza-cyclododecane-1,4,8,11-tetraacetic acid (TETA), 4,11-bis (carboxymethyl)-1,4,8,11-tetraazabicyclo[6.6.2]hexadecane (CB-TE2A), diethylenetriaminepentaacetice acid (DTPA) and 1,4,7,10-tetra-azacyclodecanetetraacetic acid (DOTA). Other chelators are useful in the method of the present invention.

The method of the present invention concentrates the therapeutic and diagnostic agent at the targeted organ or tissue. In some embodiments, the concentration of the therapeutic or diagnostic agent at the first location of the targeted organ or tissue is greater than the concentration elsewhere in the patient.

The first binding agent can be linked to the biocompatible solid support by any suitable means known to one of skill in the art. For example, the first binding agent can be linked to the biocompatible solid support via a covalent or an ionic bond. Alternatively, the first binding agent can be intercalated in the matrix of the biocompatible solid support where the second binding agent can bind to the first binding agent present on the surface of the biocompatible solid support or interior portions of the biocompatible solid support.

In some embodiments, the first binding agent can be covalently linked to the biocompatible solid support. The first binding agent can covalently bind directly to the biocompatible solid support or indirectly via the use of a linker. Any suitable linker can be used in the present invention to link the binding agent to the biocompatible solid support or the therapeutic or diagnostic agent. Representative linkers can have about 10 to about 100 linking atoms, and can include ethylene-oxy groups, amines, esters, amides and ketone functional groups. Other linkers useful in the methods of the present invention can have from about 10 to about 50 linking atoms, or from about 25 to about 50 linking atoms. Representative linkers include, but are not limited to, those shown below:

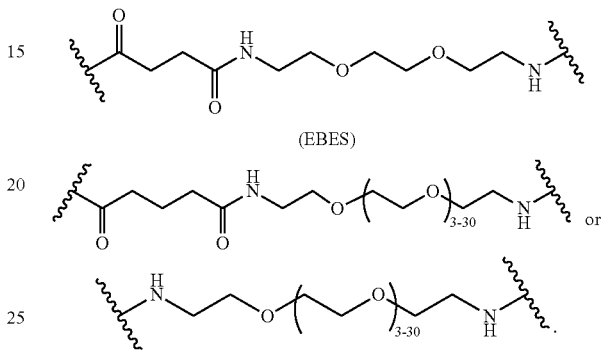

The biocompatible solid support and therapeutic or diagnostic agent can be modified with any suitable reporter or probe binding agent using a suitable linker, such as those show below:

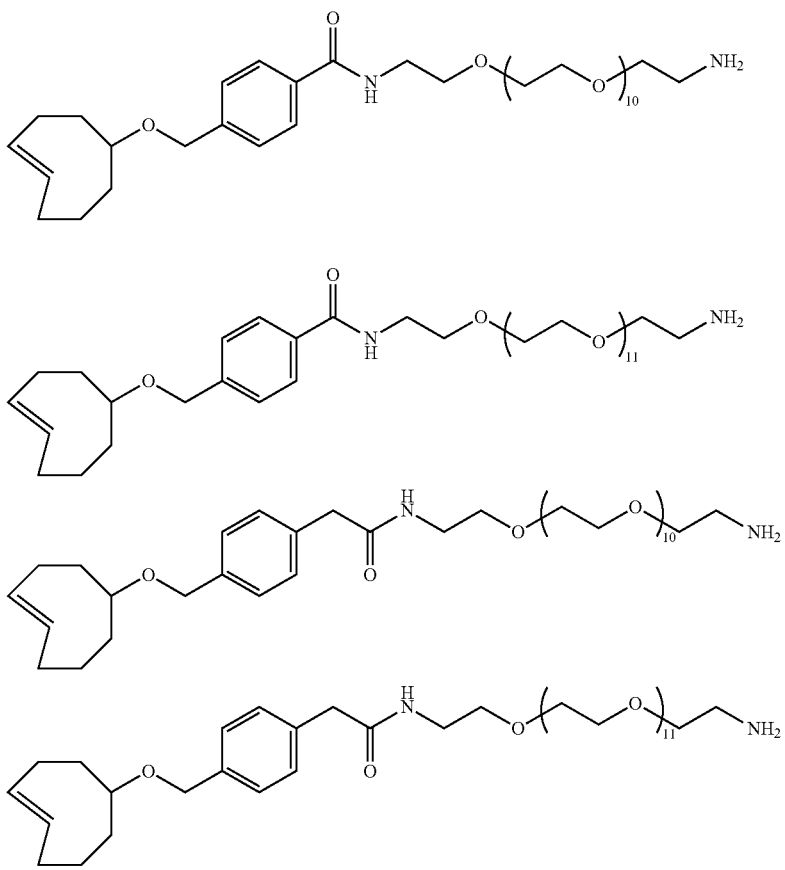

-continued
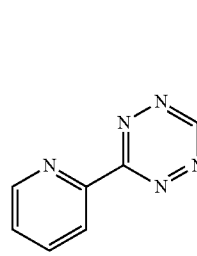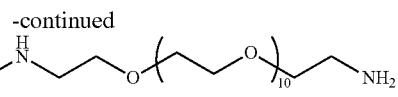
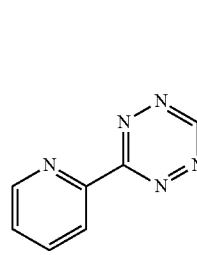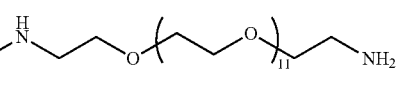
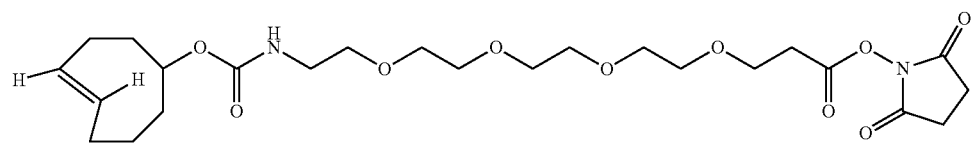
TCO-PEG4-NHS Ester I
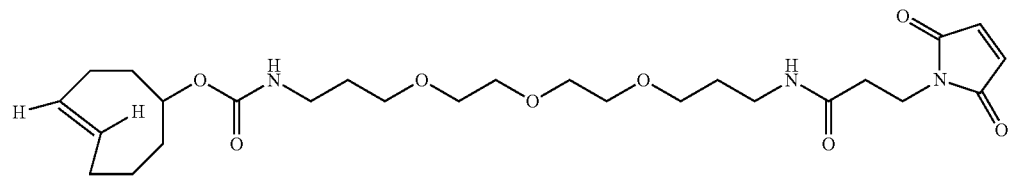
TCO-PEG3-Maleimide III
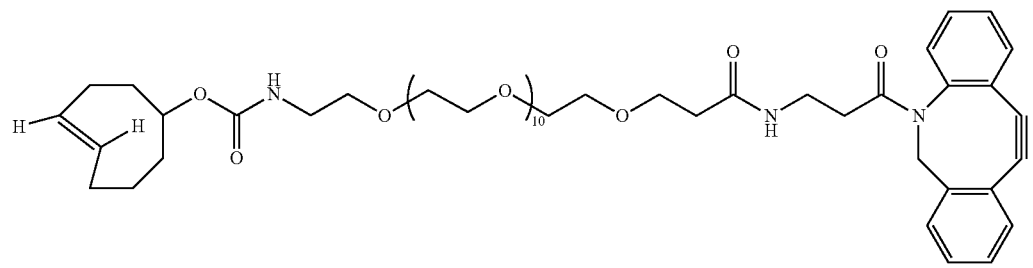
TCO-PEG12-DBCO V
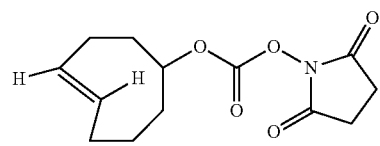
TCO-NHS Ester II
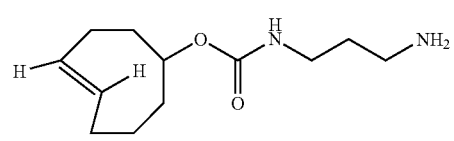
TCO-Amine IV
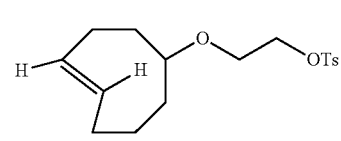
TCO-Tosyl VI
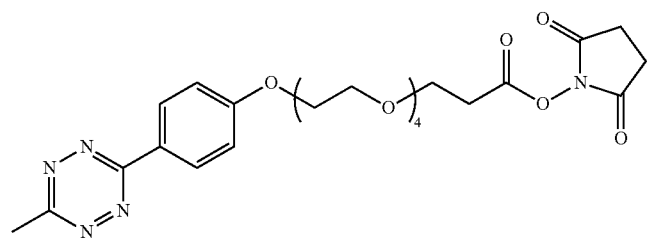
Tetrazine-PEG4-NHS Ester VII -continued
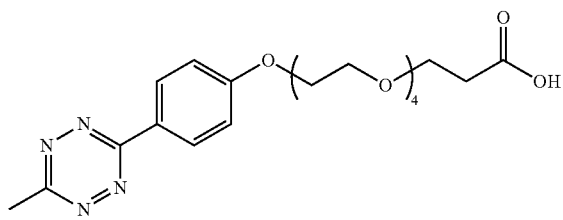
Tetrazine-PEG4-Acid IX
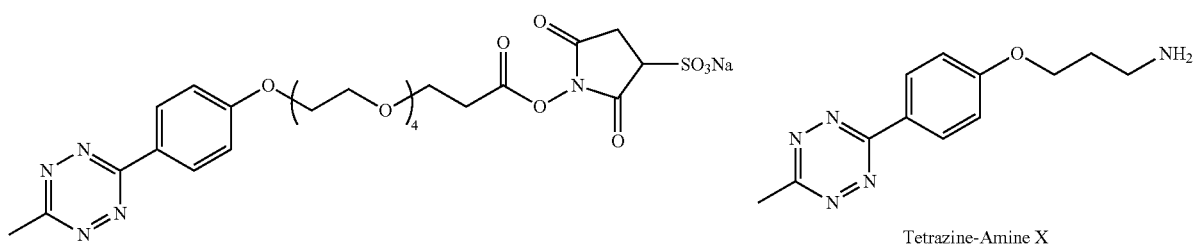
Tetrazine-Sulfo-NHS Ester VIII
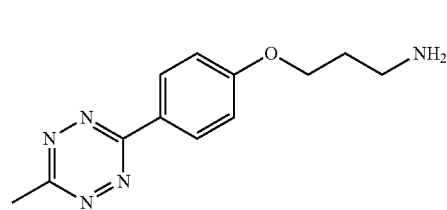
Tetrazine-Amine X
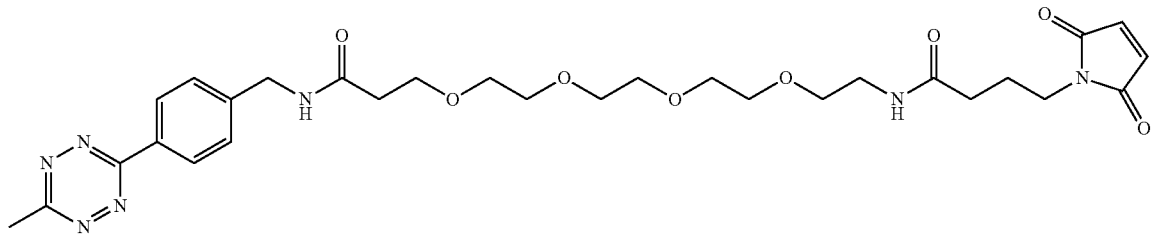
Tetrazine-PEG4-Maleimide XI
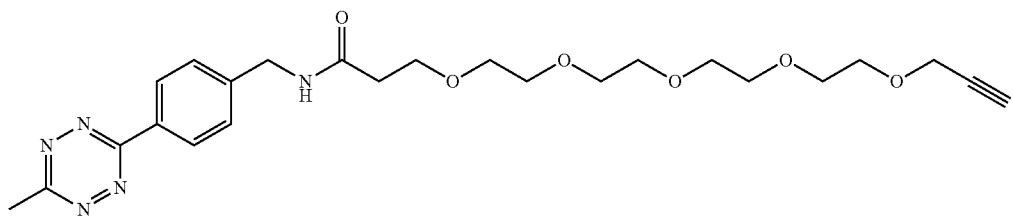
Tetrazine-PEG4-Alkyne XII
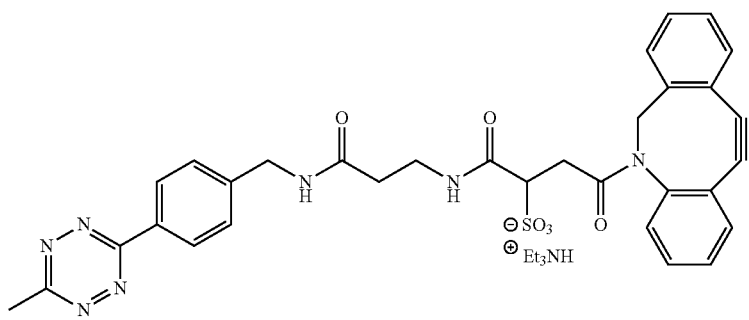
Tetrazine-DBCO XIII
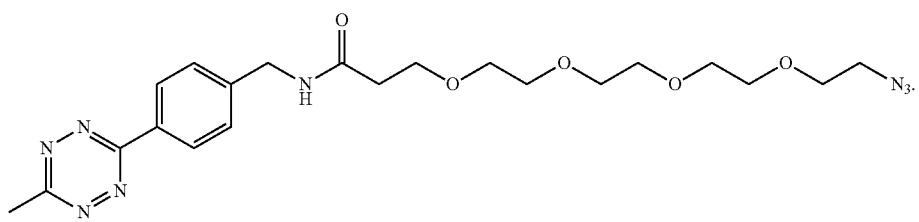
Tetrazine-PEG4-Azide XIV When using the reporter and probe binding agents of the present invention, the biocompatible solid support can be modified by any means known to one of skill in the art. For example, covalent modifications can esterify any carboxylic acids that are present, convert alcohols to ethers or esters, or convert acids or amines to amides, as shown below:

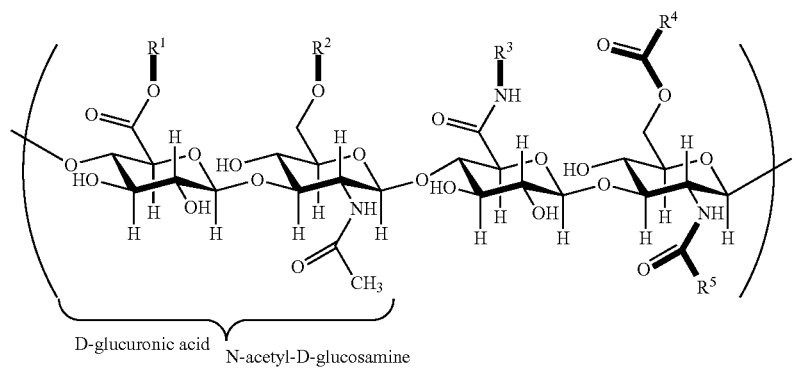

wherein $R^1$, $R^2$, $R^3$, $R^4$ and $R^5$ can be any suitable linker and binding group. Other modifications of the biocompatible solid support can include carboxymethyl modification of hydroxy or amino groups.

The biocompatible solid support can be implanted by any means known to one of skill in the art.

The therapeutic or diagnostic agent can be administered in any suitable amount sufficient to treat the disease or condition the patient is suffering from. The dose, frequency and timing of such administering will depend in large part on the selected therapeutic agent, the nature of the condition being treated, the condition of the subject including age, weight and presence of other conditions or disorders, the formulation being administered and the discretion of the attending physician. Generally, the therapeutic or diagnostic agents are administered in dosages ranging from about 2 mg up to about 2,000 mg per day, although variations will necessarily occur depending, as noted above, on the disease target, the patient, and the route of administration. The therapeutic or diagnostic agents of the present invention can be administered as frequently as necessary, including hourly, daily, weekly or monthly. The therapeutic or diagnostic agents utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, can be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time, but is typically lower than the dose required to treat the patient without having implanted the biocompatible solid support that concentrates the therapeutic or diagnostic agent at the organ or tissue requiring treatment. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage can be divided and administered in portions during the day, if desired. Doses can be given daily, or on alternate days, as determined by the treating physician. Doses can also be given on a regular or continuous basis over longer periods of time (weeks, months or years).

IV. Method of Treating

The present invention provides a method of treating a disease or condition in a patient using the method described above. In some embodiments, the present invention provides a method of treating a disease or condition in a patient, including administering to the patient a therapeutic agent linked to a first binding agent, such that when the first binding agent contacts a second binding agent at the site of the disease or condition, the first and second binding agents bind to one another forming a therapeutically effective amount of the therapeutic agent at the site of the disease or condition, wherein the amount of the therapeutic agent administered to the patient is less than the therapeutically effective amount administered to the patient in the absence of the second binding agent.

Any disease or condition can be treated using the method of the present invention. Representative diseases or conditions include, but are not limited to, cancer, autoimmune disorders, genetic disorders, infections, inflammation, neurological disorders, and metabolic disorders, or any combination. In some embodiments, the disease or condition can be an infection or an inflammation, or any combination. In some embodiments, the disease or condition can be osteomyelitis.

The disease or condition can be treated by any suitable therapeutic agent, such as those described above. In some embodiments, the therapeutic agent can be vancomycin.

V. Compositions

The present invention also provides reporter compositions for implantation in the patient, and probe composition for administration to the patient and binding to the reporter composition. In some embodiments, the present invention provides a composition including a biocompatible solid support and at least one cyclooctene linked to the biocompatible solid support.

As discussed above, the biocompatible solid support can be any suitable solid support. In some embodiments, the solid support can be a hydrogel. In some embodiments, the solid support can be alginate.

The reporter composition of the present invention can optionally include a linker. In some embodiments, the present invention provides a composition including a biocompatible solid support, at least one cyclooctene, and a linker, covalently linking each cyclooctene to the biocompatible solid support. The linker can be any suitable linker, as discussed above. In some embodiments, the linker can have the following structure:

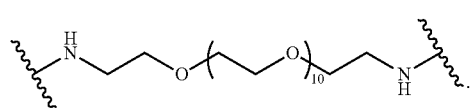

In some embodiments, the reporter composition can have the structure of the formula:

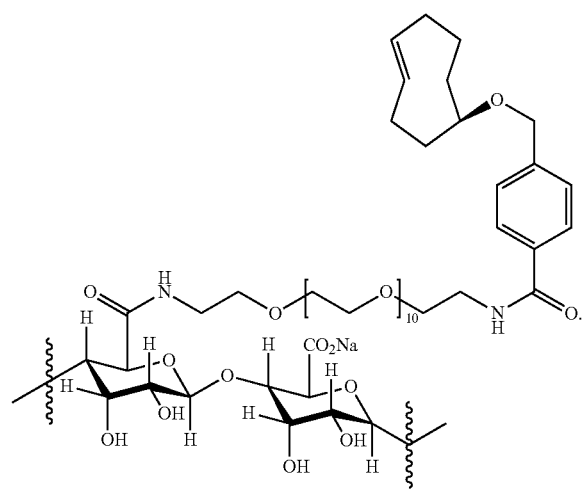

The present invention also provides probe compositions for administration to the patient. The probe compositions can have a binding agent complementary to the binding agent of the reporter composition so that when the probe composition comes into contact with the reporter composition, the binding agents react to form a covalent bond. In some embodiments, the present invention provides a composition including a therapeutic or diagnostic agent, a 1,2,4,5-tetrazine, and a linker, covalently linking the therapeutic or diagnostic agent to the 1,2,4,5-tetrazine.

Any suitable therapeutic or diagnostic agent can be used in the probe compositions of the present invention, as discussed above. Representative therapeutic agents include vancomycin. Representative diagnostic agents include DOTA-$^{64}$Cu or DOTA-$^{111}$In. In some embodiments, the composition can have the structure:

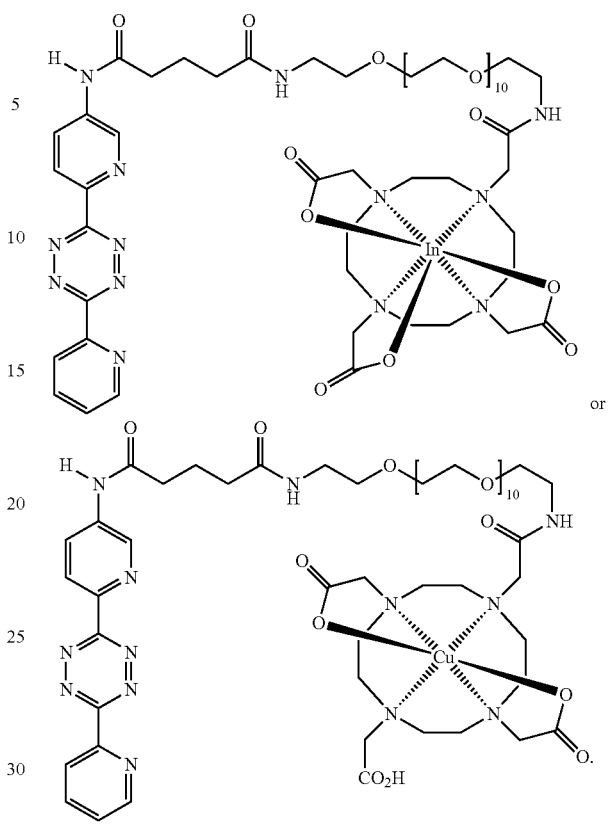

The compounds of the present invention can be prepared by a variety of methods known to one of skill in the art. For example, representative probe compositions can be prepared as shown in FIG. 1, where Compound 1, a modified tetrazine, can be synthesized as previously described (Fox, J. M.; Hassink, M., Blackman, M.; Li, Z.; Conti, P. S. PCT/US2011/044814; WO 2012/012612). Reaction of 1 with the protected linker 2 under amide forming conditions results in intermediate 3. Following deprotection of the protecting group to form 4, the therapeutic or diagnostic agent can be linked to 4, thus forming the probe compound 5.

Figure 2:
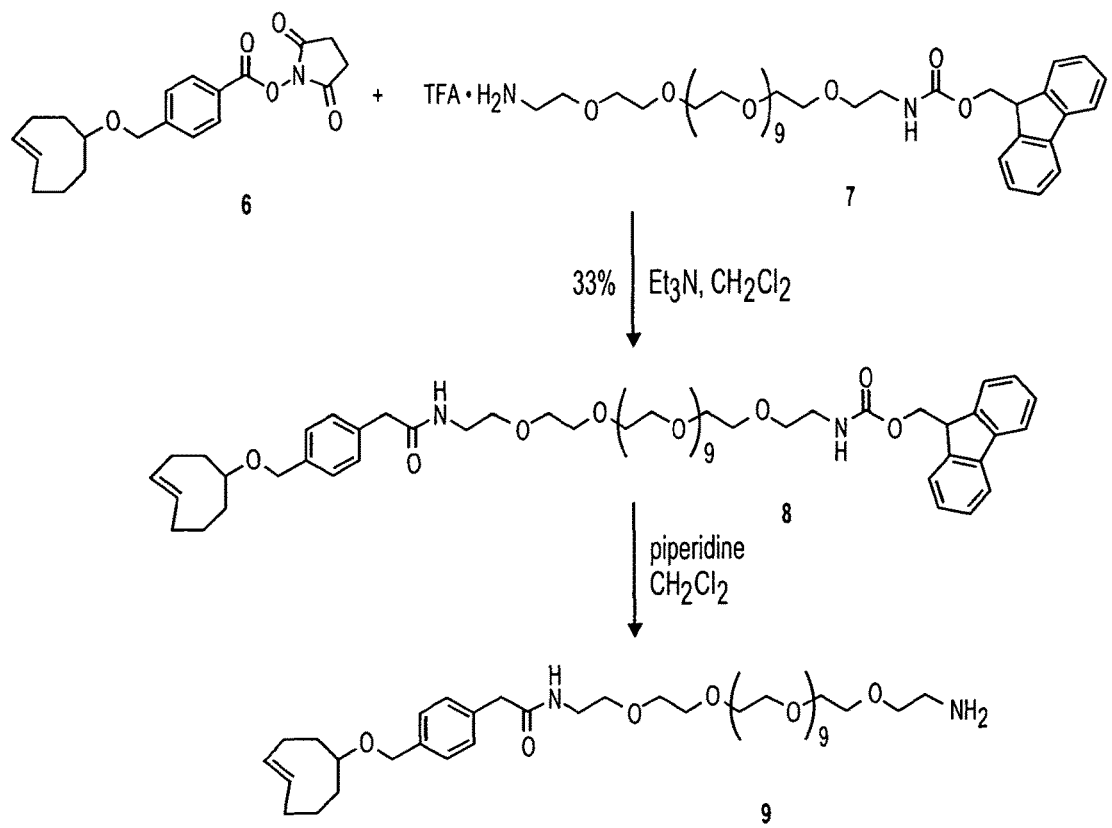
FIG. 2 shows the preparation of the cyclooctene-linker component 9.
Figure 3:
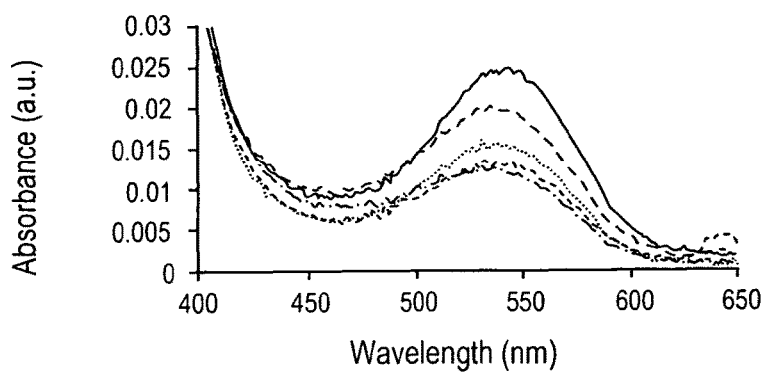
FIG. 3 shows absorption spectra of 0.1 mM 1 in DMF (top line at 550 nm). Addition of 0.5 equivalents of 9 resulted in a gradual decrease of the absorption band at 540 nm. The decrease is no longer observed upon addition of the 1.5 equivalents of 9 (bottom two lines at 550 nm), thereby suggesting that the product 9 contains no more than 33% of the cis-cyclooctene isomer.
Figure 4:
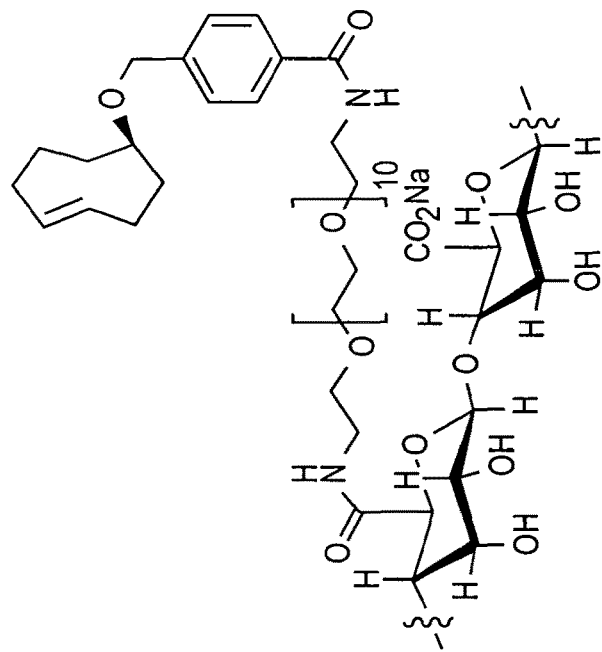
FIG. 4 shows modification of alginate hydrogel with trans-cyclooctene (TCO).
Figure 4:
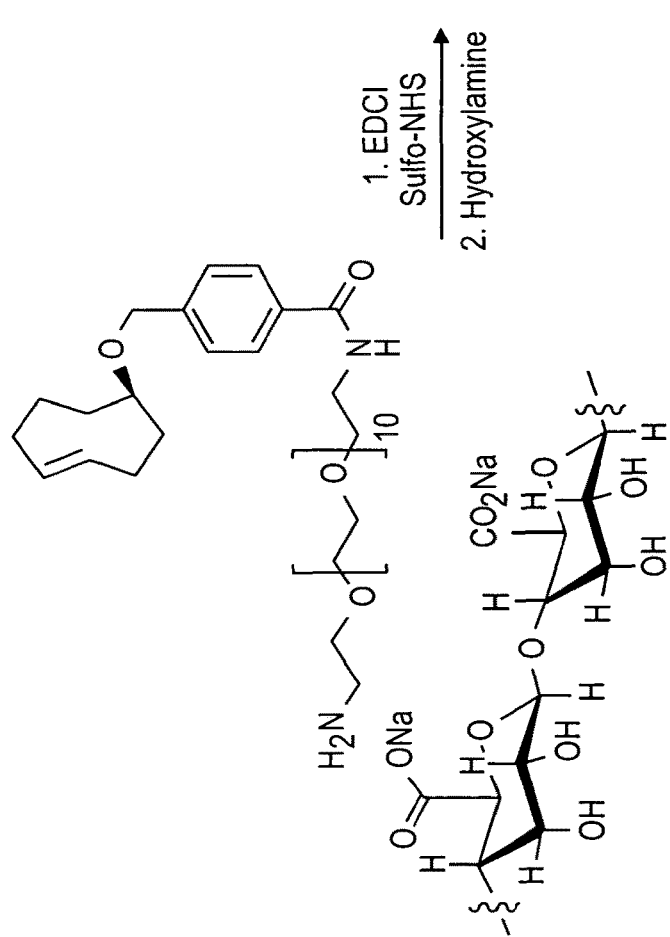
Figure 5:
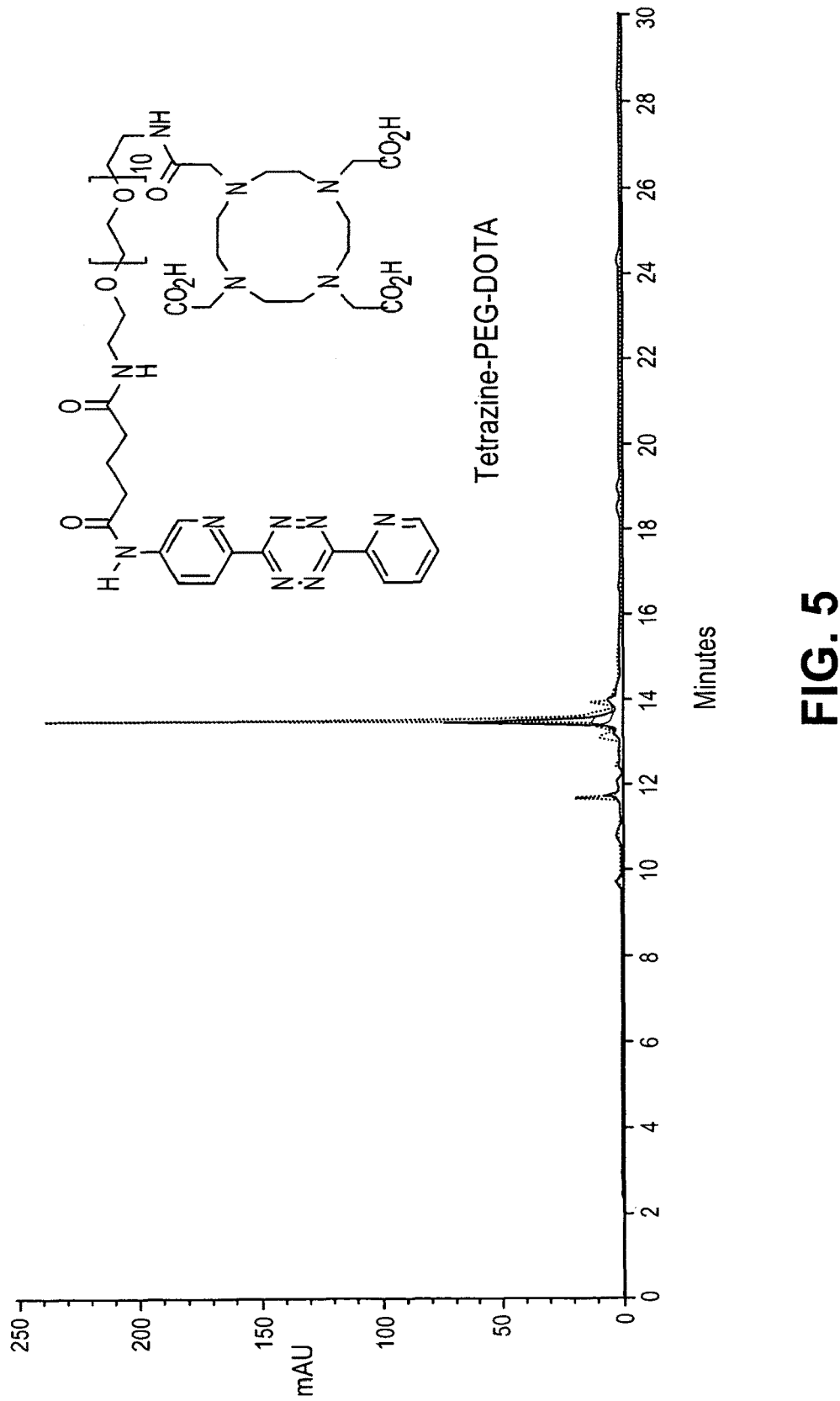
FIG. 5 shows RP-HPLC trace of starting material tetrazine 5.
Figure 6:
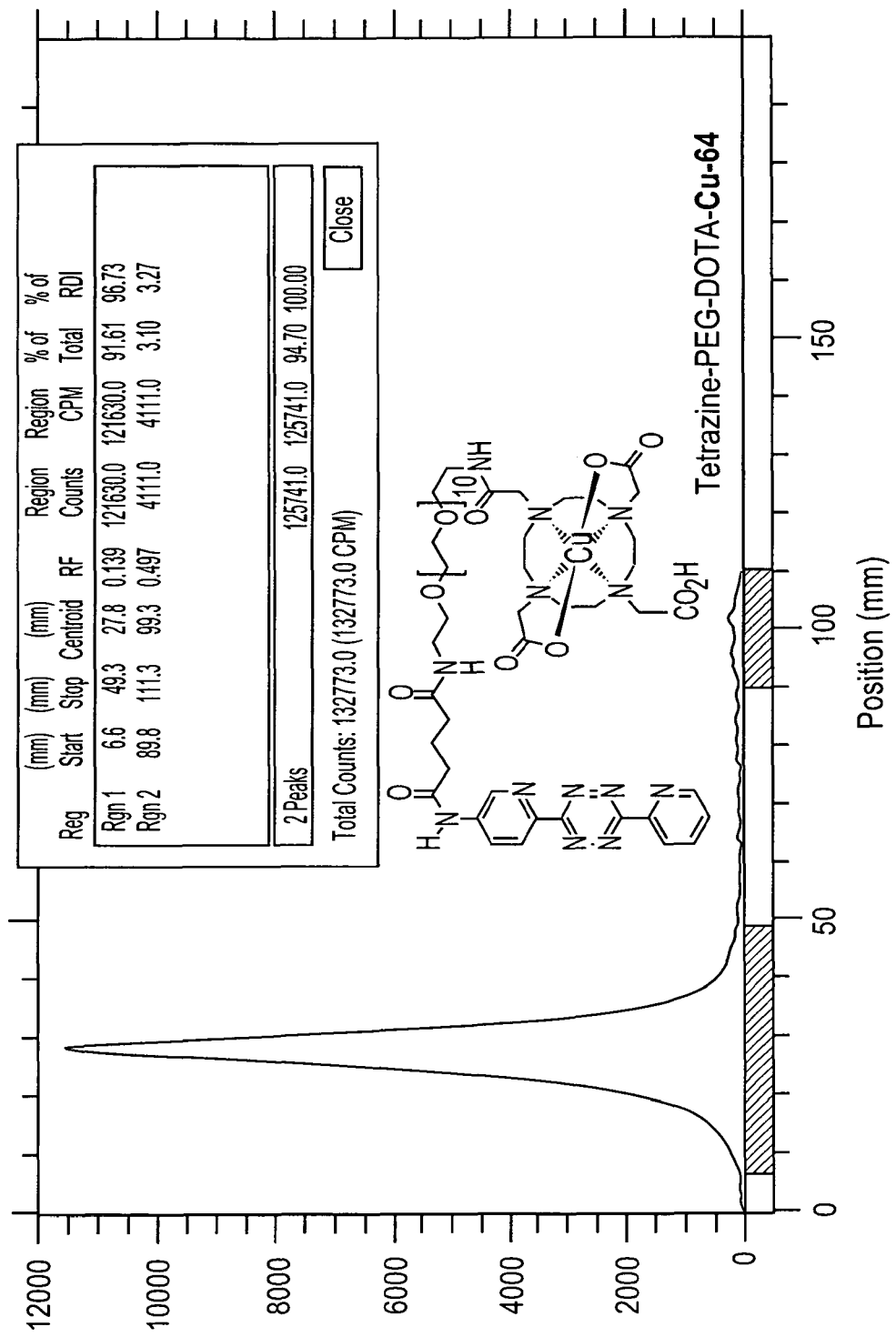
FIG. 6 shows crude radio-ITLC trace of $^{64}$Cu-tetrazine 5 reaction mixture.
Figure 7:
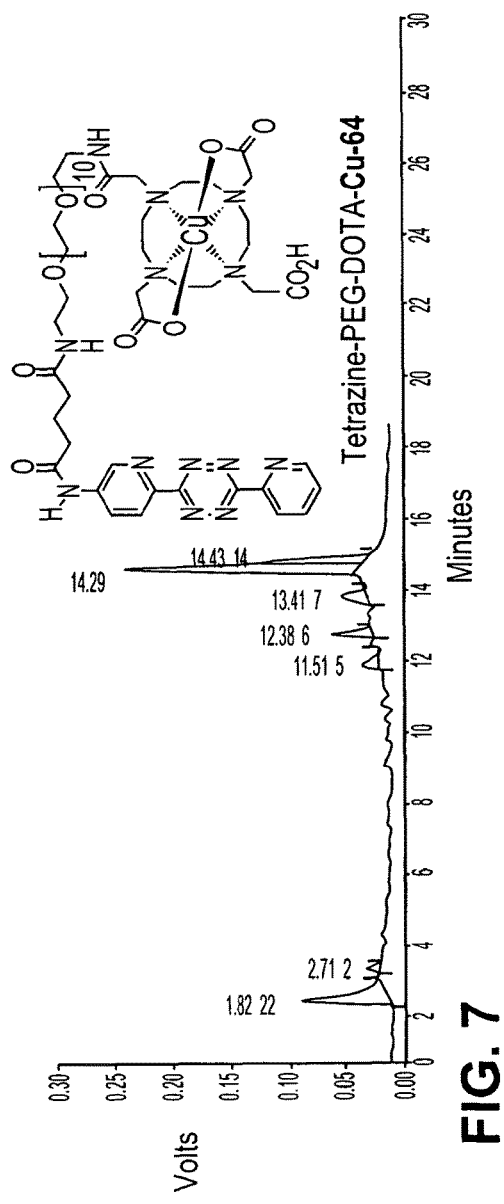
FIG. 7 shows crude radio-RP-HPLC trace of $^{64}$Cu-tetrazine 5 reaction mixture.
Figure 8:
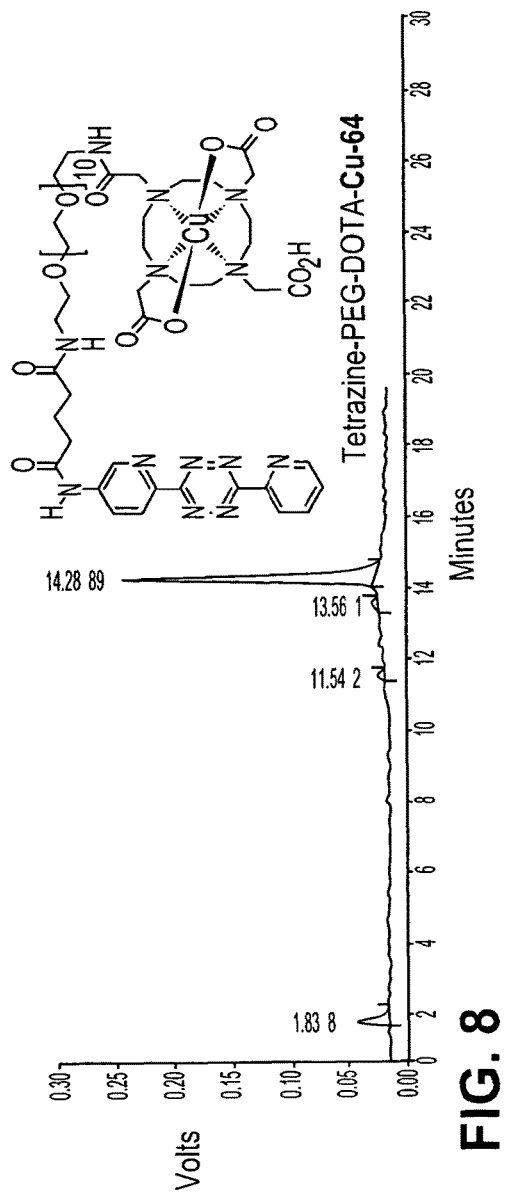
FIG. 8 shows radio-RP-HPLC Trace after RP-HPLC purification of $^{64}$Cu-tetrazine 5.
Figure 9:
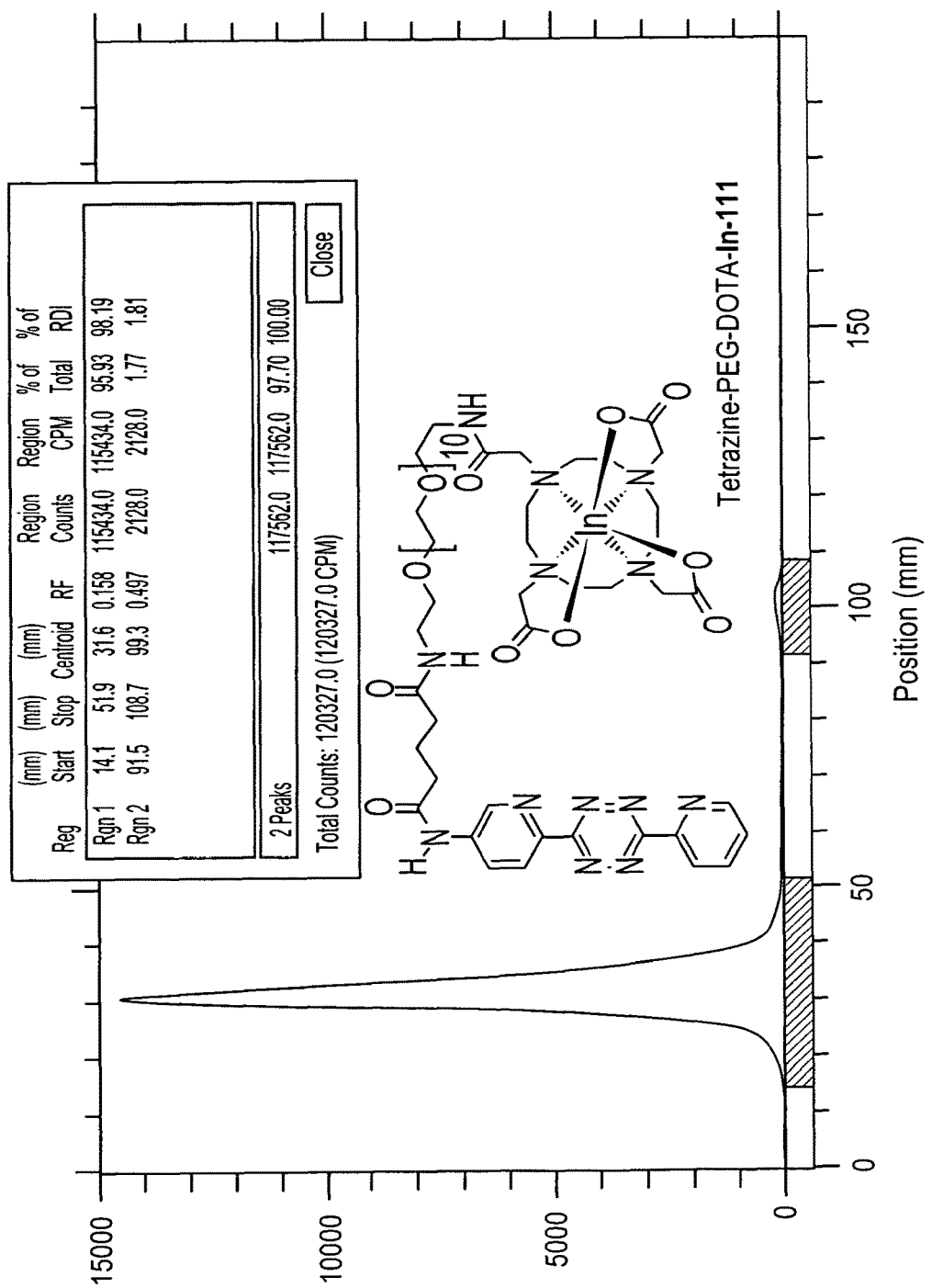
FIG. 9 shows crude ITLC trace of $^{111}$In-tetrazine 5 reaction mixture.
Figure 10:
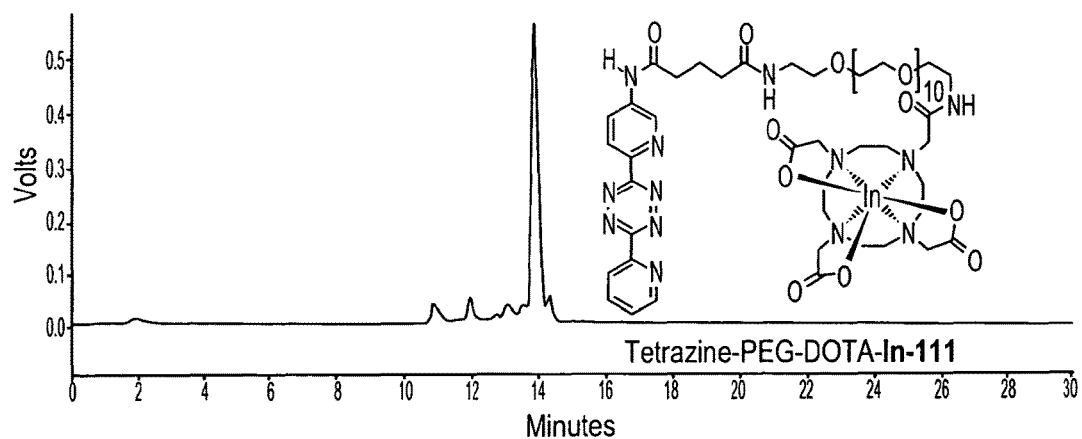
FIG. 10 shows crude Radio-HPLC trace of $^{111}$In-tetrazine 5 reaction mixture.
Figure 11:
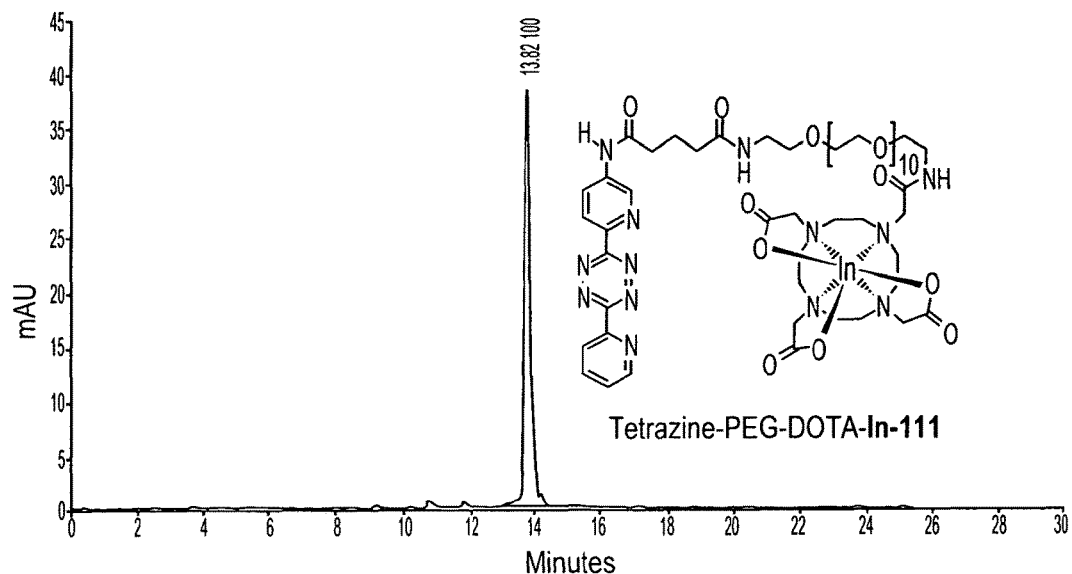
FIG. 11 shows radio-HPLC Trace after HPLC purification of $^{111}$In-tetrazine 5.
Figure 12:
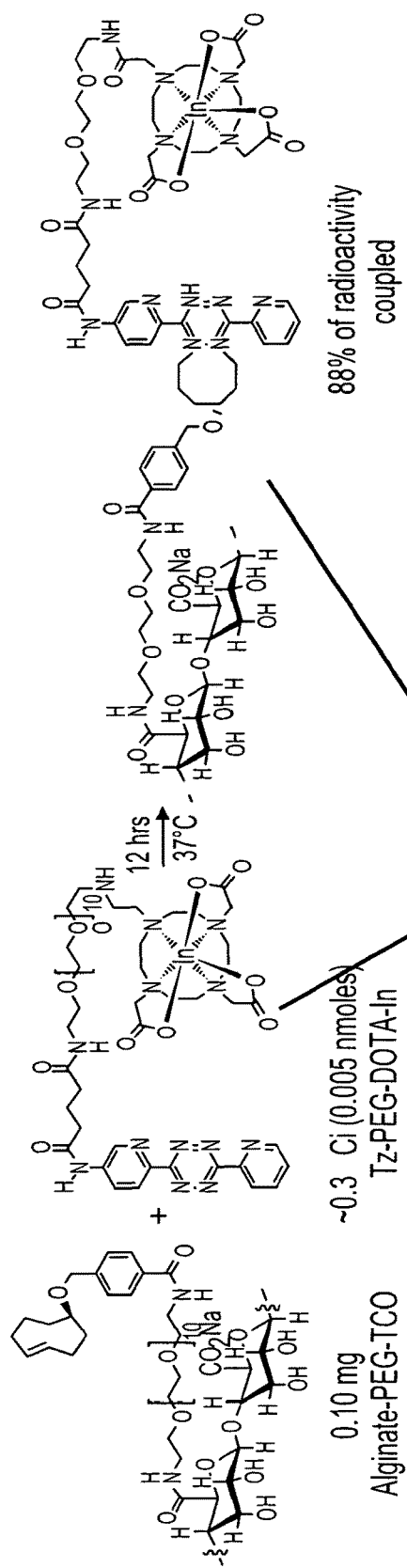
FIG. 12 shows size exclusion HPLC spectrum indicating uptake of radioactivity by TCO-gel.
Figure 12:
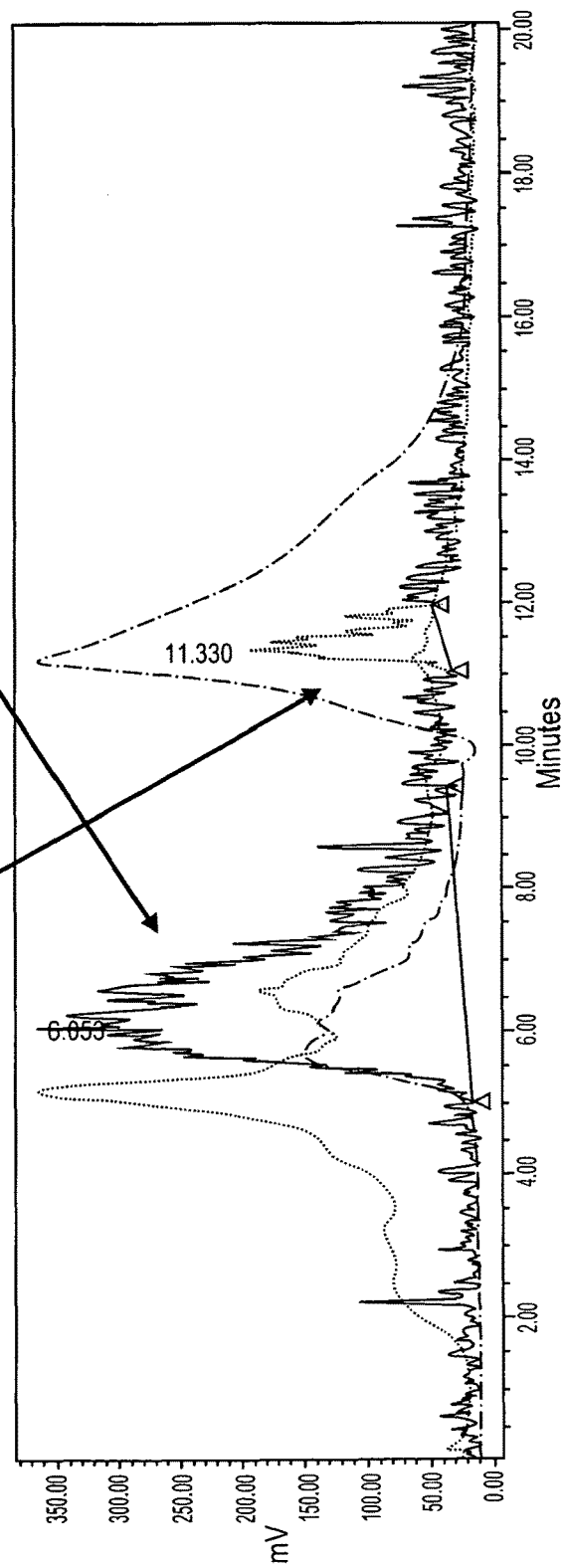
Figure 13:
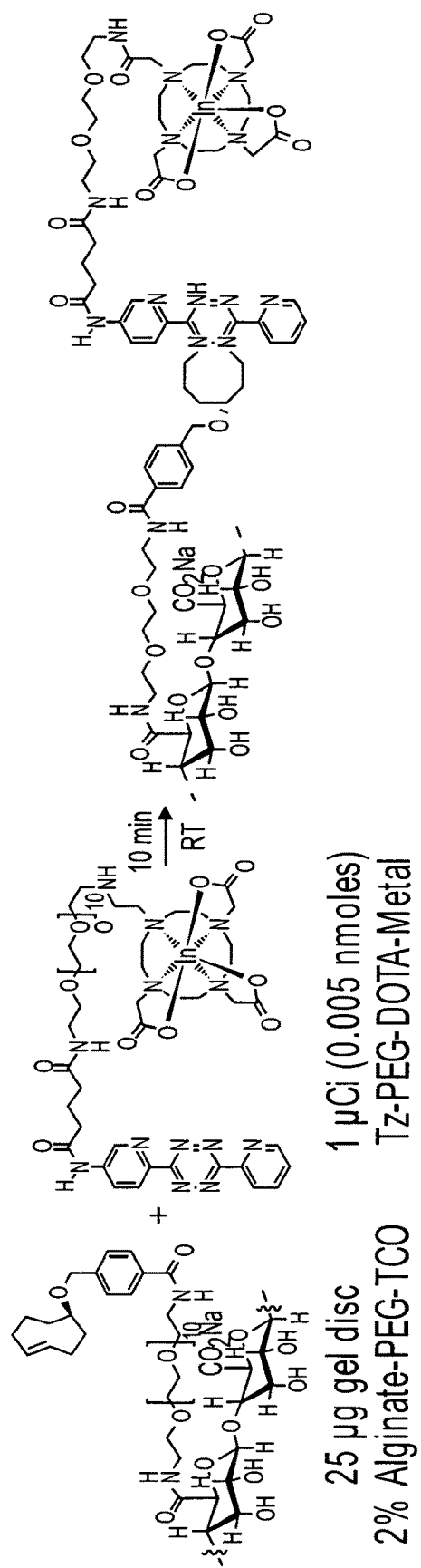
FIG. 13 shows conjugation of the alginate-PEG-TCO and the tetrazine-PEG-DOTA-metal.
Figure 14:
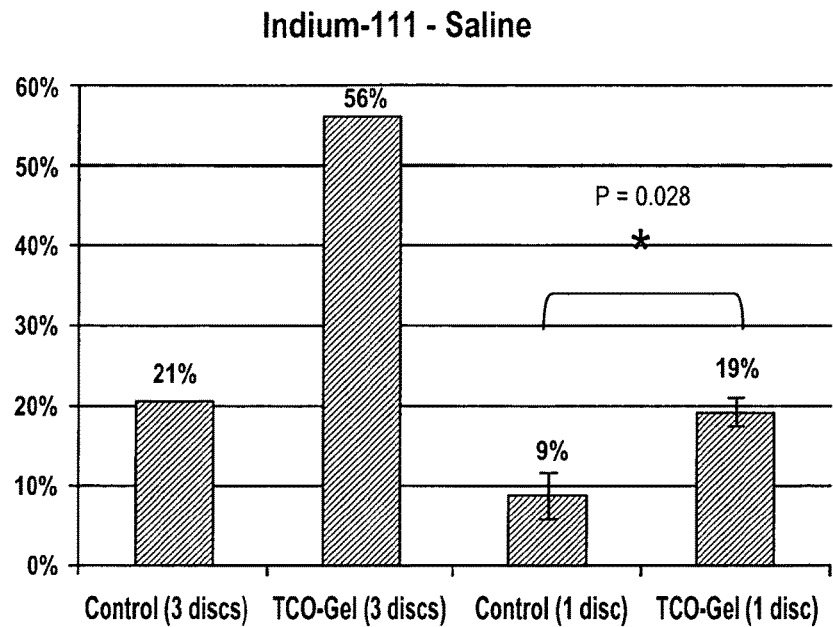
FIG. 14 shows in vitro studies with discs indicating increase in uptake of radioactivity at experimental group.
Figure 15:
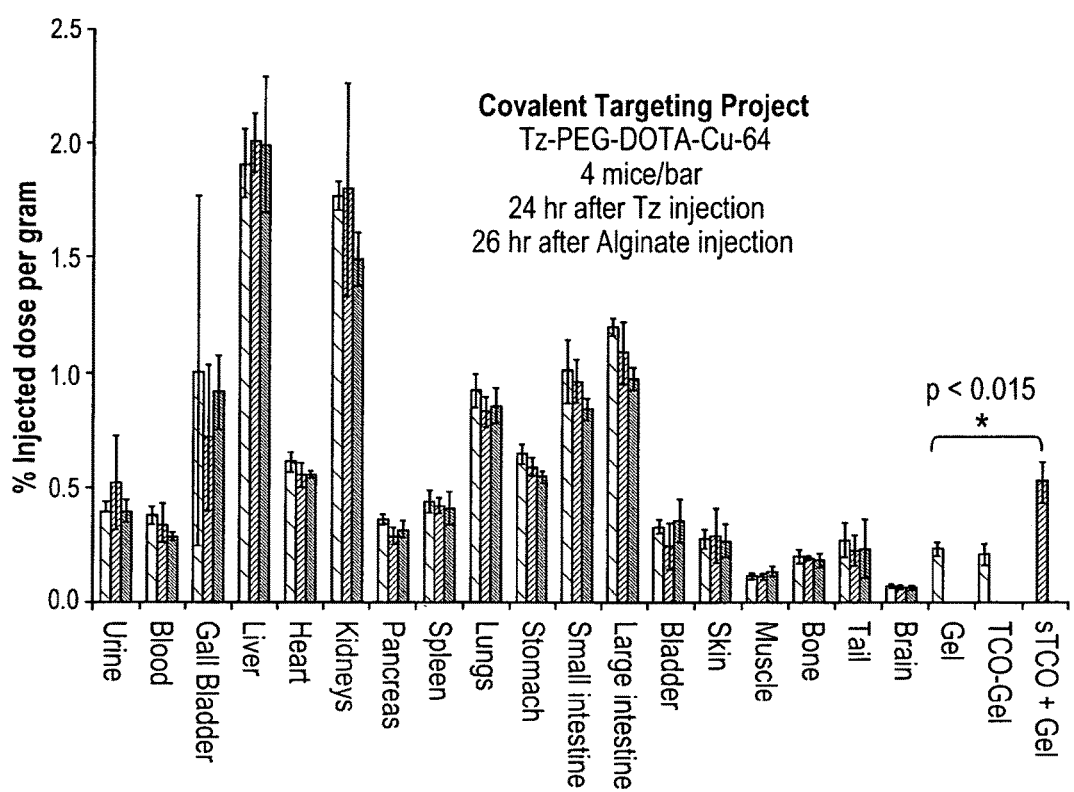
FIG. 15 shows biodistribution of $^{64}$Cu-tetrazine 5 at 24 hours after tetrazine injection.
Figure 16:
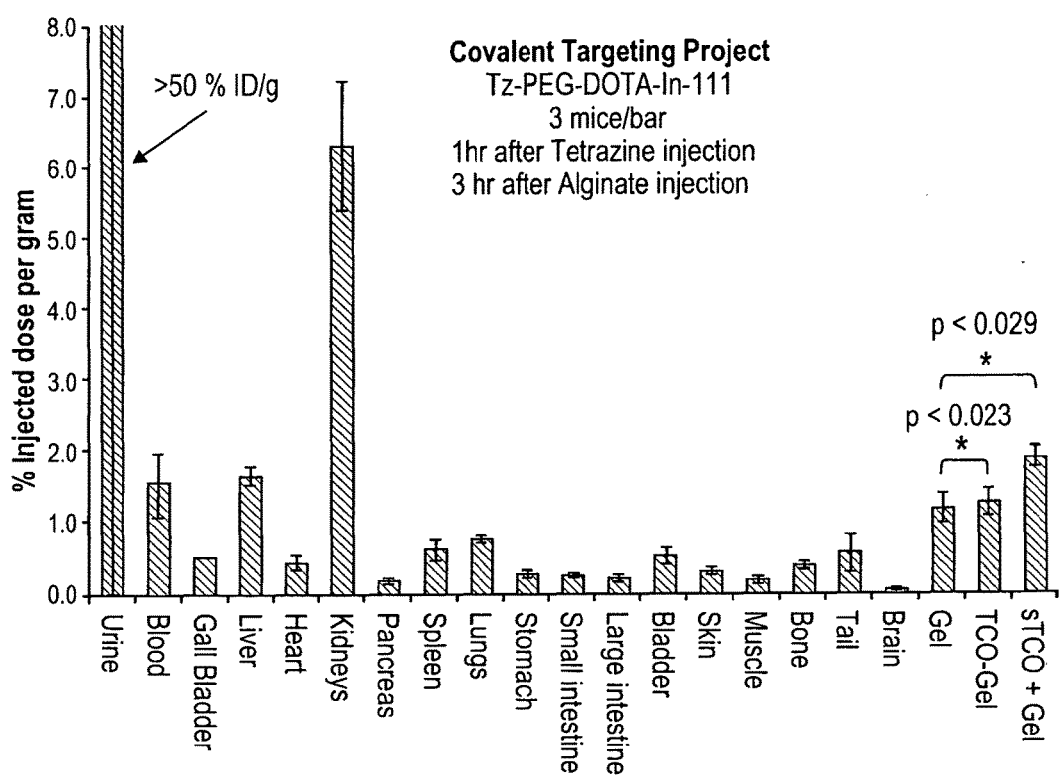
FIG. 16 shows biodistribution of $^{111}$In-tetrazine 5 at 1 hour time point after tetrazine injection.
Figure 17:
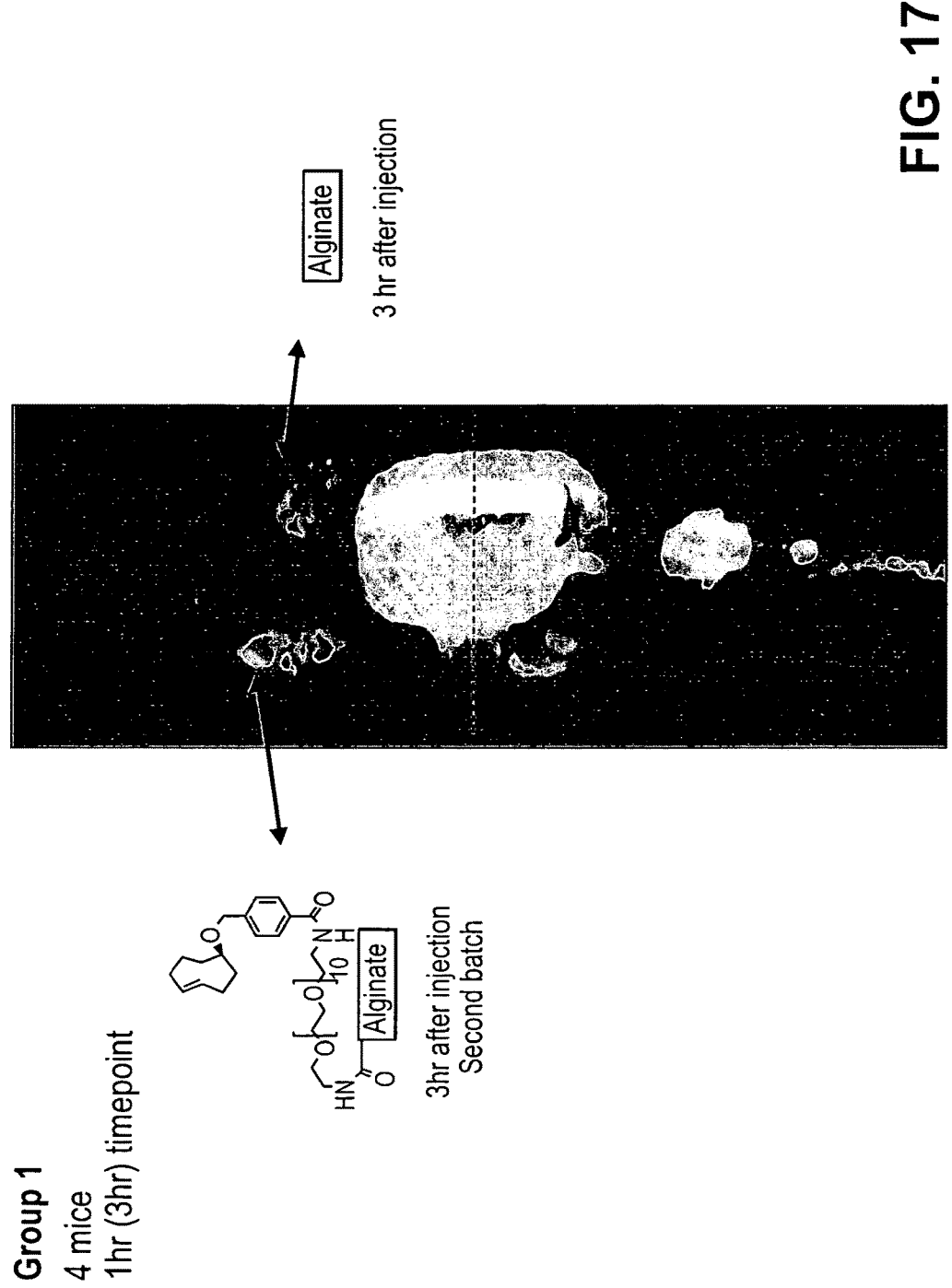
FIG. 17 shows CT images of mice receiving $^{64}$Cu-tetrazine 5 (0.09-0.21 mCi).
Figure 18:
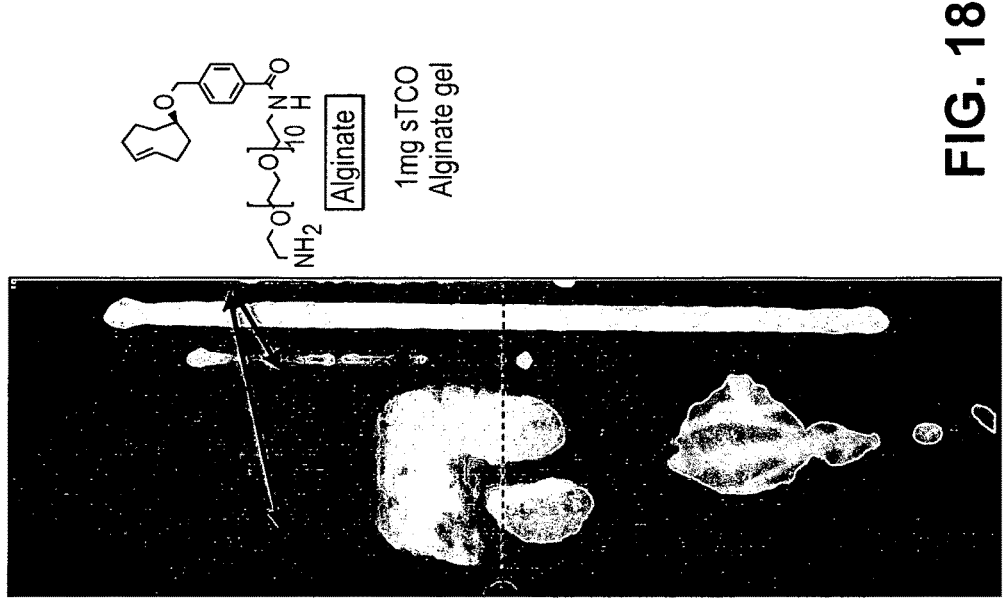
FIG. 18 shows CT images of mice receiving $^{64}$Cu-tetrazine 5 (0.09-0.21 mCi).
Figure 18:
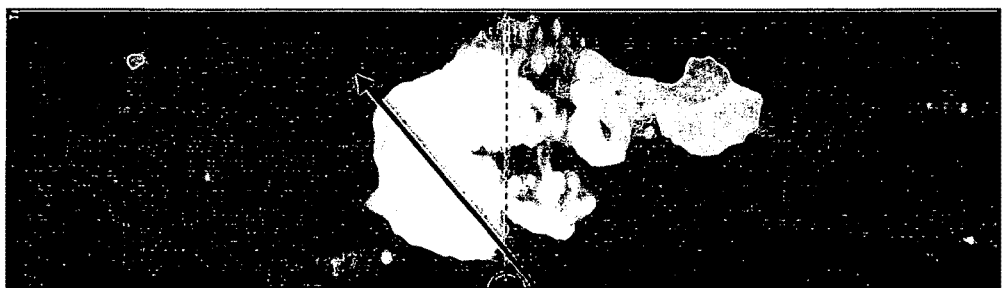
Figure 18:
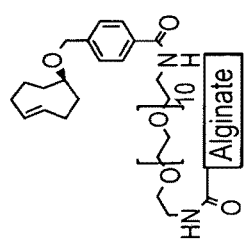
Figure 18:
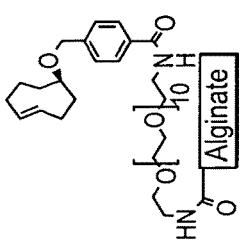
Figure 19:
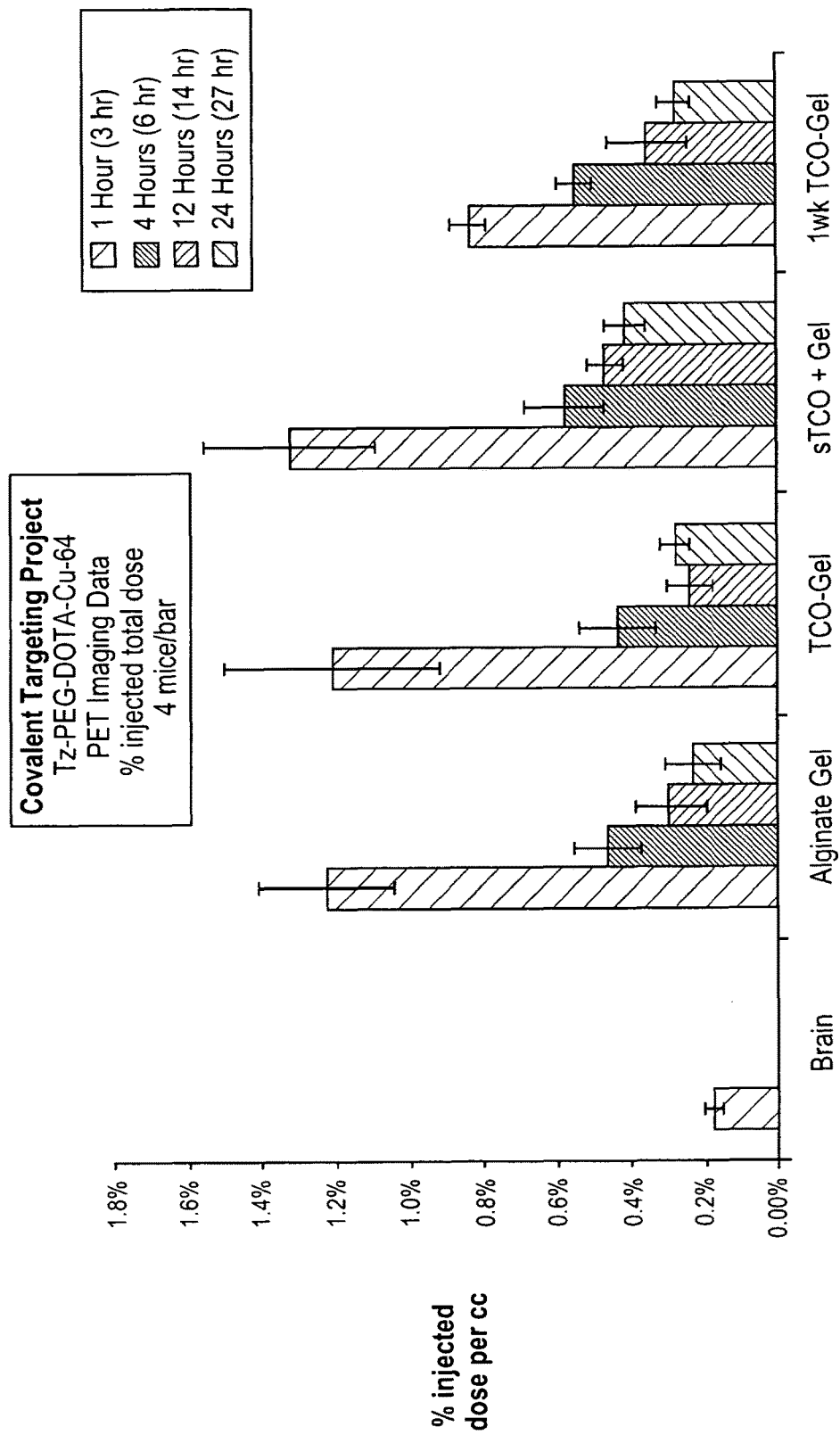
FIG. 19 shows Analysis of Imaging Data from $^{64}$Cu-tetrazine 5 injection by ROI and measurement of activity (absolute % of injected dose).
Figure 20:
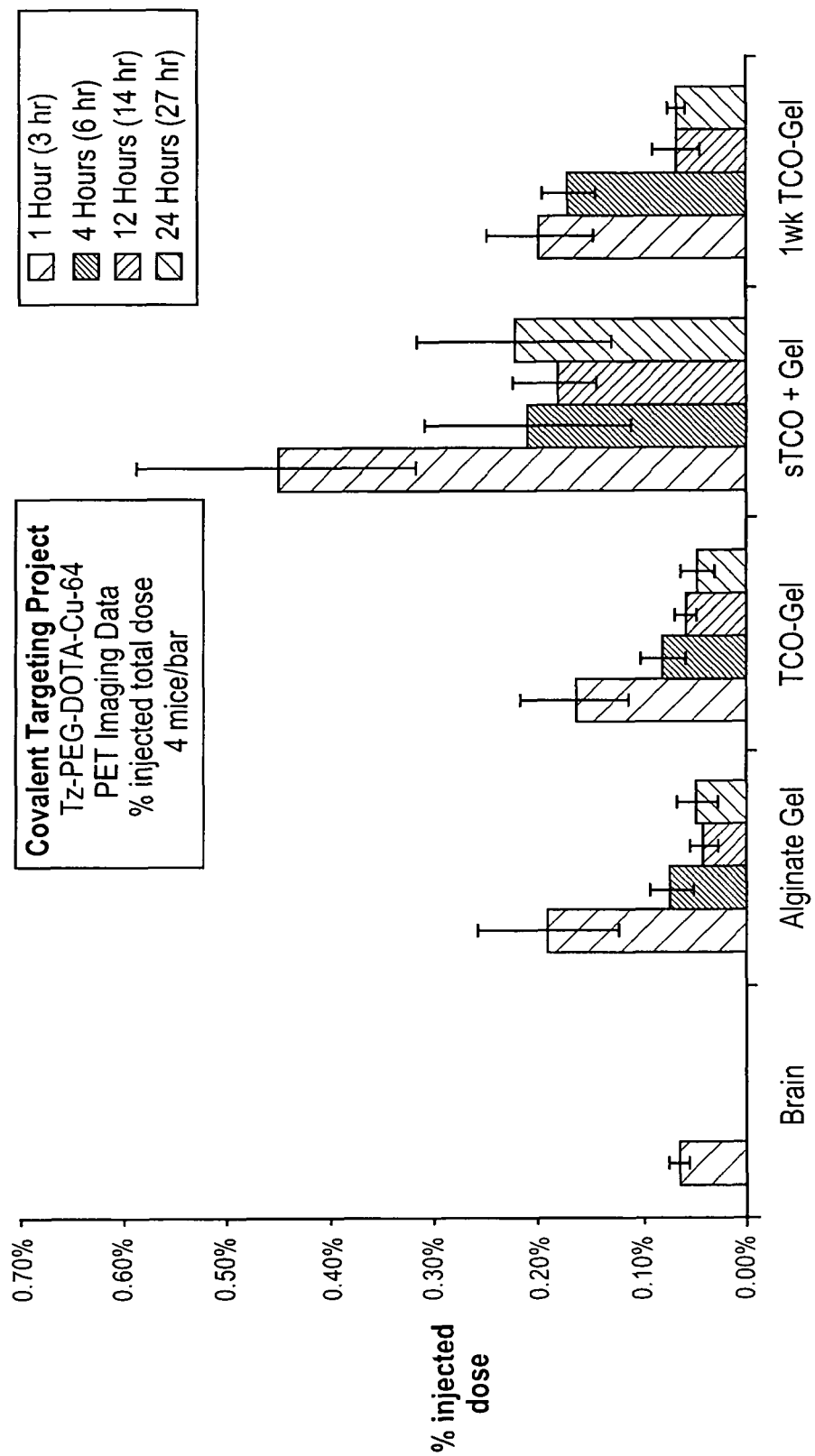
FIG. 20 shows Analysis of Imaging Data from $^{64}$Cu-tetrazine 5 injection by ROI and measurement of activity (absolute % of injected dose).

The reporter compositions are prepared similarly. For example, as shown in FIG. 2, Compound 6, which can be synthesized as previously described, can be linked to a protected linker under standard amide forming conditions to form 8, which is then deprotected to form 9. The reporter composition is then formed as described in FIG. 4 by reaction of 9 with the biocompatible solid support, alginate, for example.

The methods of making the compounds of the present invention can include any suitable protecting group or protecting group strategy. A protecting group refers to a compound that renders a functional group unreactive to a particular set of reaction conditions, but that is then removable in a later synthetic step so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006, which is incorporated herein by reference in its entirety.

VI. Formulation

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the compounds of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

VII. Administration

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

VIII. Examples

All reagents and NMR solvents were purchased from Sigma-Aldrich (St. Louis, Miss.), unless otherwise noted. Compound 2 was obtained from Iris Biotech (Marktredwitz, Germany), while compound 8 was purchased from Polypure (Oslo, Norway). DOTA-NHS ester was obtained from Macrocyclics (Dallas, Tex.). Silica gel was purchased from Silicycle (Quebec, Canada), while preparative TLC plates (20×20 cm; 1000 μm in thickness) were purchased from Analtech (Newark, Del.). Ultrapure alginates were purchased from ProNova Biomedical (Norway). [$^{111}$In] Indium chloride solutions was purchased from PerkinElmer (Waltham, US). [$^{64}$Cu] Copper chloride in dilute HCl was purchased from Washington University (St. Louis, Mo.) or was produced in-house by the 64Ni(p,n)64Cu nuclear reaction using an 11 MeV Siemens RDS 111 cyclotron and purified by anion exchange chromatography (Biorad AG 1-X8). Dulbecco's Phosphate Buffered Saline (DPBS) was purchased from Invitrogen Corporation (Carlsbad, Calif.).

NMR experiments were carried out in $CDCl_3$ or [$D_6$] DMSO, using a Varian 400 MHz VNMRS machine. High resolution ESI mass spectrometry data was obtained using Agilent Ion Trap LC/MSD SL at Boston University Chemical Instrumentation Center measured either in the positive or negative. During the organic synthesis phase, an Agilent 1100 Series system equipped with a Waters XBridge C18

Column (19×250 mm) applying a gradient of water and MeCN containing 0.1% TFA was used for HPLC purification.

During radiochemistry and for in-vivo analyses and purifications, reversed-phase HPLC was performed using a Beckman-Colter System Gold 128 (Brea, Calif.) chromatography systems equipped with Jupiter Proteo C-12 columns (250×4.6 mm, 4 μm, Phenomenex, Torrance, Calif.) and single wavelength or diode array UV detectors (set to 220 & 254 nm) connected in series to a Bioscan FlowCount photomultiplier tube (PMT) (Bioscan, Washington, D.C.). Data was analyzed using the 32 Karat software package (Beckman-Colter). Mobile phase consisted of Solvent A: 0.05% trifluoroacetic acid in water and Solvent B: 100% acetonitrile, a flow rate of 1.5 mL/min, and a linear gradient beginning at 2 min after injection from 9% Solvent B then increasing to 81% over a 30 min period unless otherwise stated.

During in-vitro experiments using alginate gel, molecular sieving high performance liquid chromatography (HPLC) was performed on a Waters Breeze chromatography system with a Waters 2487 dual absorbance detector (220 & 320 nm) and a Bioscan Flow-count radioactivity detector. A Phenomenex BioSep SEC-53000 column (7.8×300 mm) was eluted in isocratic 0.1 M sodium phosphate, pH 6.8, at 1.0 mL/min.

The $^{64}$Cu and $^{111}$In-labeling yields were determined by radio-TLC, using ITLC-SG strips (Pall Life Sciences, Ann Arbor, Mich.) eluted with 200 mM EDTA in 0.9% aq. NaCl and performed using a Bioscan 200 imaging scanner (Bioscan, Washington D.C.). In these conditions, free radionuclides migrate with Rf=0.9, while radionuclides attached to tetrazine 6 remain at the origin.

PET/CT data was acquired using an Inveon Preclinical Imaging Station (Siemens Medical Solutions.

Animal Handling.

All animals were handled in accordance with a protocol approved by the University of California, Davis, Animal Use and Care Committee.

Statistical Analysis.

Group variation is described as the mean±one standard deviation. Single groups were compared with a two-tailed unpaired t test. Groups with P<0.05 were considered significantly different. Microsoft Excel version 12.8.9 was used for all statistical calculations.

Example 1. Tetrazine Modified Diagnostic Agent (5)

Tert-butyl (37,41-dioxo-41-((6-(6-(pyridin-2-yl)-1,2, 4,5-tetrazin-3-yl)pyridin-3-yl)amino)-3,6,9,12,15,18, 21,24,27,30,33-undecaoxa-36-azahentetracontyl) carbamate (3)

Dissolved 2 (0.39 g, 0.61 mmol) in DMF (15 mL). To the stirring solution of 2 in DMF, sequentially added 1 (0.20 g, 0.55 mmol), Benzotriazol-1-yloxytris(Demethylamino) phosphonium hexafluorophosphate (BOP) (0.25 g, 0.55 mmol) and triethylamine (0.55 g, 5.5 mmol). The reaction mixture was stirred at room temperature, under nitrogen atmosphere for 18 h. The solvent was removed under low vacuum and the title product was purified by gravity silica column using a gradient of MeOH in CH$_2$Cl$_2$ (0-10%). Yield=0.40 g (74%). The NMR spectra matched the one previously published (Rossin, R.; Verkerk, P. R.; van den Bosch, S. M.; Vulders, R. C. M.; Verel, I.; Lub, J.; Robillard, M. S. *Angew. Chem. Int. Ed.* 2010, 49, 3375. Mooney, 1999).

N1-(2-(2-(2-(2-(2-(2-(2-(2-(2-(2-(2-aminoethoxy) ethoxy)ethoxy)ethoxy)ethoxy)ethoxy) ethoxy)ethoxy)ethoxy)ethox)ethyl)-N5-(6-(6-(pyridin-2-yl)-1,2,4,5-tetrazin-3-yl)pyridin-3-yl) glutaramide (4)

Compound 3 was dissolved in a 5:1 mixture of CH$_2$Cl$_2$: TFA (10 mL) and stirred at room temperature for 2 h. The solution turned from pink to deep red. The solvents were removed and the product was azeotroped with MeOH (2×20 mL). The crude product was carried over to the next step without further purification. $^1$H NMR (CDCl$_3$) δ 10.36 (s, 1H), 9.37 (s, 1H), 9.26 (bs, 1H), 9.01 (s, 1H), 8.91 (d, J=7.8 Hz, 1H), 8.81 (d, J=8.6 Hz, 1H), 8.61 (d, J=8.1 Hz, 1H), 8.39 (t, 8.0 Hz, 1H), 7.95 (t, J=5.0 Hz, 1H), 7.50 (s, 1H), 6.94 (bs, 3H), 3.72-3.08 (m, 35H), 2.51 (t, J=4.6 Hz, 2H), 2.36 (t, J=6.0 Hz, 2H), 1.99 (t, J=6.7 Hz, 2H), 1.26 (t, J=7.3 Hz, 7H). $^{13}$C NMR (CDCl$_3$) δ 175.27, 173.06, 161.32, 161.17, 159.42 (q, J=39.5 Hz, TFA), 147.52, 145.94, 142.85, 140.89, 139.13, 138.48, 130.81, 128.95, 126.65, 125.97, 115.2 (q, J=287.5 Hz, TFA), 70.13, 70.09, 70.05, 69.98, 69.92, 69.88, 69.77, 69.72, 69.66, 69.55, 69.49, 69.38, 69.35, 69.26, 68.82, 66.52, 46.59, 39.61, 35.63, 34.67, 29.59, 21.21, 8.38. HRMS: C$_{41}$H$_{66}$N$_9$O$_{13}$ [M+H$_2$O] calcd. 892.4702 (different from value listed on Data), found 892.4739.

2,2',2''-(10-(2,40,44-trioxo-44-((6-(6-(pyridin-2-yl)-1,2,4,5-tetrazin-3-yl)pyridin-3-yl)amino)-6,9,12,15, 18,21,24,27,30,33,36-undecaoxa-3,39-diazatetratetracontyl)-1,4,7,10-tetraazacyclododecane-1,4,7-triyl) triacetic acid (5)

DOTA-NHS ester (100 mg, 0.131 mmol) was added to a solution of 4 (129 mg, 0.131 mmol) and triethylamine (179 μL, 1.31 mmol) in DMF (5 mL). The reaction mixture was stirred at room temperature for 4 h. The solvent was removed under reduced pressure. The crude product was dissolved in water, containing 0.1% TFA (2 mL) and filtered through 0.45 μm Polyvinylidene fluoride membrane (PVDF). The title product was purified by preparative HPLC using a gradient of H$_2$O (0.1% TFA) and CH$_3$CN (0.1% TFA). Yield 78 mg (47%). The NMR spectra matched the one previously published (Rossin, R.; Verkerk, P. R.; van den Bosch, S. M.; Vulders, R. C. M.; Verel, I.; Lub, J.; Robillard, M. S. *Angew. Chem. Int. Ed.* 2010, 49, 3375. Mooney, 1999).

HRMS: C$_{57}$H$_{91}$N$_{13}$O$_{20}$ calcd. 1278.6503, found 1278.6580.

Example 2. Preparation of TCO Conjugate 4-(((S,E)-cyclooct-4-enyloxy)methyl)-(N-(9H-fluoren-9-yl)methyl carbamate)-N-(2-(2-(2-(2-(2-(2-(2-(2-(2-(2-aminoethoxy)ethoxy)ethoxy)ethoxy) ethoxy)ethoxy)- ethoxy)ethoxy)ethoxy)ethoxy) ethoxy)ethyl)benzamide (8)

Compound 7 (0.15 g, 0.58 mmol) was dissolved in CH$_2$Cl$_2$ (10 mL) in a 100 mL round bottom flask. A solution of 7 (0.50 g, 0.58 mmol) in CH$_2$Cl$_2$ (10 mL) was added, followed by triethylamine (0.3 mL, 2.3 mmol). The reaction mixture was stirred for 18 h at room temperature under nitrogen atmosphere. The solvents were then removed and the title product was purified by gravity silica column using a 1:20 MeOH:CH$_2$Cl$_2$ solution as an eluent. Yield=0.19 g (33%). $^1$H NMR (CDCl$_3$) δ 7.75 (t, J=7.9 Hz, 2H), 7.68 (d, J=7.4 Hz, 2H), 7.54 (d, J=7.3 Hz, 2H), 7.34 (d, J=7.8 Hz, 2H), 7.30 (d, J=7.7 Hz, 2H), 7.23 (t, J=7.4 Hz, 2H), 5.65-5.39 (m, 2H), 4.43 (dd, J$_1$=14.4 Hz, J$_2$=5.2 Hz, 2H), 4.32 (d, J=6.8 Hz, 2H), 4.14 (t, J=6.9 Hz, 1H), 3.59-3.34 (m, 48H), 2.33-1.21 (m, 10H). $^{13}$C NMR (CDCl$_3$) δ 167.33, 156.25, 143.90, 142.96, 141.18, 135.78, 133.26, 131.20, 127.54, 127.04, 126.93, 126.64, 125.01, 119.83, 74.14, 70.40, 70.25, 69.81, 66.43, 50.56, 47.25, 40.08, 39.68, 34.47, 32.81, 29.78, 27.56.

4-(((S,Z)-cyclooct-4-enyloxy)methyl)-N-(2-(2-(2-(2-(2-(2-(2-(2-(2-(2-(2-aminoethoxy)ethoxy)ethoxy)ethoxy)ethoxy)ethoxy)ethoxy)ethoxy)ethoxy)ethoxy)ethyl)benzamide (9)

Piperidine (2.5 mL) was added dropwise to a solution of 8 (193 mg, 0.19 mmol) in CH$_2$Cl$_2$ (10 mL). The resulting solution was stirred at room temperature for 4 h. The solvents were removed and the title product was puried by gravity silica column using a 1:10 MeOH:CH$_2$Cl$_2$ solution as an eluent. Yield=86 mg (57%). $^1$H NMR (CDCl$_3$) δ 7.73 (t, J=7.9 Hz, 2H), 7.36-7.28 (m, 2H), 6.96 (bd, J=7.5 Hz, 1H), 5.65-5.40 (m, 2H), 5.30-5.26 (m, 1H), 4.54-4.33 (m, 3H), 3.60-3.36 (m, 48H), 3.06-2.99 (m, 1H), 2.40-1.44 (m, 10H). HRMS: C$_{40}$H$_{70}$N$_2$O$_{13}$ calcd. 787.4878, found 787.4938.

Example 3. Alginate Chemical Modification with 9

MVG alginate, a high G-containing alginate (M:G ratio of 40:60 as specified by the manufacturer) were used in all of the studies. Using previously described carbodiimide chemistry the carboxylic acids within high M- and high G-containing alginates were modified with trans-cyclooctene 9. All reactions were performed in 25 mL 0.1M 2-(N-morpholino)ethanesulfonic (MES) acid buffer containing 0.3M NaCl at pH 6.5 with 250 mg of alginate, a concentration of 1% (w/v). 12.1 mg (0.063 mmol) of 1-ethyl-3-(3-dimethylaminopropyl)carbodiimide (EDC) was added to the alginate to activate the carboxylic acids along the polymer chain at a 1:20 molar ratio to the uronic acid monomers of the alginate. 6.9 mg (0.032) of N-hydroxysulfosuccinimide (sulfo-NHS) was added as a coreactant at a 1:2 molar ratio to EDC. The amine 9 (10 mg, 0.013 mmol) was added to the reaction in 1 mL of MES buffer, and the alginates were allowed to react for 20 h. The modified alginates were purified with extensive dialysis (MWCO 3500) over 5 days. The alginate was then removed from the dialysis tubing and filtered using a 0.22 µm Millipore Sterile filters into 25 mL conical vials. Then the alginate was frozen by placing it in the fridge for 1 hr, then −20° C. freezer for 2 hr, and finally −80° C. freezer overnight. The samples were then placed in the lyophilizer until completely dry (5-10 days) and then stored at −80° C. until needed.

When ready for use, calcium cross-linked alginate hydrogels was diluted to a 2.5% (v/v) alginate solutions in ddH2O containing 0.25% (w/v) PBS. A sterile super-saturated calcium sulfate solution was made at a concentration of 0.21 g CaSO4/ml ddH2O. About 0.4 ml of the slurry was added for every 10 ml of 2.0% alginate solution.

For in-vivo use, the alginate gel solution and the super-saturated calcium sulfate solution mentioned above were mixed rapidly in the syringes through a double female connector and immediately injected into the animal.

For in-vitro experiments, the alginate gel solution and the super-saturated calcium sulfate solution mentioned above were mixed rapidly through a double female connector in the syringes. Then the 2% alginate gelling solution was cast between parallel glass plates with 2 mm spacers to prepare gel films. Hydrogel discs were punched out of the film with a hole punch (McMaster-Carr, Chicago, Ill.).

The exact same protocol was used for the ionically bonded group except that trans-cyclooctene 9 was not added with EDC and sulfo-NHS, but added at a later step, with the super-saturated calcium sulfate solution. For the control group no trans-cyclooctene 9 was added at any point of the sequence.

Example 4. In Vitro Experiments

Tetrazine Copper Radiolabeling.

$^{64}$Cu-chloride (5-10 µL in 0.5 M HCl) was diluted with 0.1 M ammonium acetate buffer (pH 7, 50-100 µL). The DOTA-conjugated tetrazine (5) was dissolved (1.28 mg/mL) in 0.1M ammonium acetate, pH 7.0. An aliquot of 5 was combined with a suitable amount of [$^{64}$Cu] copper chloride and incubated for 10 min at room temperature under gentle agitation. Complete incorporation of the radionuclide was monitored by radio-TLC. After HPLC purification and evaporation of the solvents under mild heat, the radiochemical purity of the $^{64}$Cu-tetrazine 5 was monitored by radio-HPLC.

For animal experiments, the $^{64}$Cu-tetrazine solution was diluted with sterile saline. The specific activity of the $^{64}$Cu-tetrazine 5 solution used for in vivo experiments was typically 3.3 MCi/g.

Example 5. Tetrazine Indium Radiolabeling $^{111}$In-chloride (5-10 µL in 0.5 M HCl) was diluted with 0.1 M ammonium acetate buffer (pH 7, 50-100 µL). The DOTA-conjugated tetrazine (5) was dissolved (1.28 mg/mL) in 0.1M ammonium acetate, pH 7.0. An aliquot of 5 was combined with a suitable amount of [$^{111}$In] indium chloride and incubated for 10 min at 37° C. under gentle agitation. Complete incorporation of the radionuclide was monitored by radio-TLC. After HPLC purification and evaporation of the solvents under mild heat, the radiochemical purity of the $^{111}$In-tetrazine 5 was monitored by radio-HPLC.

For animal experiments, the $^{111}$In-tetrazine solution was diluted with sterile saline. The specific activity of the $^{111}$In-tetrazine 5 solution used for in vivo experiments was typically 18 Ci/g.

Example 6. In Vitro Reactivity

Size Exclusion HPLC.

Compound 9 incorporation to the alginate backbone was quantified using radiolabeled tetrazine 5 as a proxy. Briefly, a 2% alginate gel solution was mixed with a known amount of tetrazine-radionuclide with a determined specific activity. The amount of radioactivity incorporated into the gel was determined through size-exclusion HPLC, whereby larger compounds (alginate gel) elute earlier than smaller compounds.

Discs.

The reactivity of alginate-TCO was tested in PBS and mouse serum. Typically, a premade disc weighing approximately 25 µg was placed in a test tube. As a control an alginate disc untreated with TCO was used. The disc was added to a saline or serum solution containing a known amount of compound 10 tagged with a radionuclide (either $^{64}$Cu-tetrazine 5 or $^{111}$In-tetrazine 5). Radioactivity was measured using a Wallac 1470 Wizard gamma counter (PerkinElmer, Inc.). The discs were then washed and vortex three times with 250 μL of saline and the radioactivity was measure again.

Example 7. In Vivo Studies

Biodistribution Experiments.

There were two biodistribution studies done. The first one was done with $^{64}$Cu-tetrazine 5, at 26 hrs after all the scans had been performed. The second biodistribution study was done with $^{111}$In-tetrazine 5 at 3 hours after subcutaneous injections of alginate gels, followed by intravenous injection of tetrazine 5.

The mice were euthanized by cervical dislocation. Organs and bodily fluids of interest, such as urine, blood, gall bladder, liver, heart, kidneys, pancreas, spleen, lungs, stomach, small intestine, large intestine, bladder, skin, muscle, bone, tail, brain were harvested as well as the experimental groups (gel, TCO-gel, sTCO+gel), all were washed with de-ionized water to remove excess blood, and weighed. Radioactivity was measured using a Wallac 1470 Wizard gamma counter (PerkinElmer, Inc.). Radioactivity uptake was presented as percent injected dose per gram (% ID/g). All values were corrected for isotope decay.

Example 8. Imaging Experiments

Mice received injections of one of the alginate experimental groups (control, TCO-Gel, sTCO+Gel) at a subcutaneous site (either right or left shoulder). About two hours later, the mice received tail vein injections with $^{64}$Cu-tetrazine 5 (0.09-0.21 mCi). At 1 h after tetrazine 5 injection, the mice were anesthetized with 1%-2% isoflurane and imaged through the PET scanner for 30 minutes, then the CT images were collected. Static images were collected for 15 or 30 min and coregistered with Inveon Research Workstation software (Siemens Medical Solutions, Memphis, Tenn.). The process was repeated at 6, 14 and 26 hrs after initial injection of alginate). PET images were reconstructed. The small-animal PET images were analyzed using the Inveon Research Workshop. Regions of interest were selected from PET images using CT anatomic guidelines, and the activity associated with them was measured with the Inveon Research Workshop software.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A composition comprising:
   an implantable biocompatible solid support selected from the group consisting of polysaccharide hydrogels, alginate, cellulose, hyaluronic acid, chitosan, chitin, chondroitin sulfate, heparin, a polymer matrix, a metal, a ceramic and a plastic;
   at least one binding agent linked to the biocompatible solid support, wherein the at least one binding agent is capable of a bioorthogonal reaction with a corresponding binding agent and the bioorthogonal reaction is between a trans-cyclooctene and a tetrazine; and
   a linker covalently linking each binding agent to the implantable biocompatible solid support.

2. The composition of claim 1, wherein the implantable biocompatible solid support comprises alginate.

3. The composition of claim 1, wherein the composition has the structure of the formula:

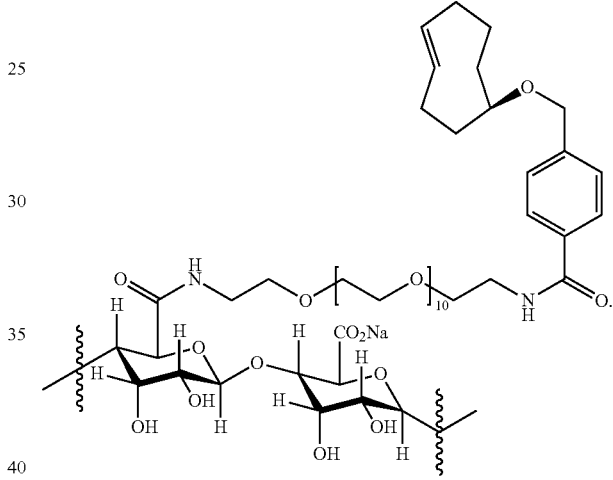

4. The composition of claim 1, wherein the implantable biocompatible solid support is selected from the group consisting of alginate, chitin, hyaluronic acid and chitosan.

5. The composition of claim 4, wherein the implantable biocompatible solid support is hyaluronic acid.

6. The composition of claim 1, wherein the composition is formulated in a sterile injectable preparation.

7. The composition of claim 1, wherein the at least one binding agent comprises trans-cyclooctene or tetrazine.

8. The composition of claim 1, wherein the at least one binding agent is trans-cyclooctene or tetrazine.

9. The composition of claim 1, wherein the implantable biocompatible solid support comprises the polymer matrix.

* * * * *